United States Patent [19]
Roth et al.

[11] Patent Number: 5,445,946
[45] Date of Patent: Aug. 29, 1995

[54] INTRAVACUOLAR STAINS FOR YEAST AND OTHER FUNGI

[75] Inventors: Bruce L. Roth, Corvallis; Paul J. Millard, Eugene; Stephen T. Yue, Eugene; Richard P. Haugland, Eugene, all of Oreg.

[73] Assignee: Molecular Probes, Inc., Eugene, Oreg.

[21] Appl. No.: 206,081

[22] Filed: Mar. 3, 1994

Related U.S. Application Data

[63] Continuation-in-part of Ser. No. 90,890, Jul. 12, 1993, which is a continuation-in-part of Ser. No. 47,683, Apr. 13, 1993, abandoned.

[51] Int. Cl.$^6$ .............. C12Q 1/04; C12Q 1/02; C12Q 1/68; C07H 17/00
[52] U.S. Cl. .................. 435/34; 435/29; 435/25; 435/4; 435/26; 435/27; 435/28; 435/6; 536/23.1; 536/22.1; 536/28.1
[58] Field of Search ............. 435/34, 29, 25, 4, 26, 435/27, 28, 6; 536/23.1, 22.1, 28, 28.1

[56] References Cited

U.S. PATENT DOCUMENTS

| | | | |
|---|---|---|---|
| 4,544,546 | 10/1985 | Wang et al. | 435/6 |
| 4,554,546 | 10/1985 | Wang et al. | 424/7.1 |
| 4,556,636 | 12/1985 | Belly et al. | 435/34 |
| 4,639,421 | 7/1987 | Sage, Jr. | 435/34 |
| 4,883,867 | 11/1989 | Lee et al. | 536/28 |
| 4,883,867 | 11/1989 | Lee et al. | 536/28 |
| 4,937,198 | 6/1990 | Lee et al. | 436/94 |
| 4,957,870 | 9/1990 | Lee et al. | 436/63 |
| 4,997,928 | 3/1991 | Hobbs, Jr. | 435/6 |
| 5,057,413 | 10/1991 | Terstappen et al. | 435/6 |
| 5,321,130 | 6/1994 | Yue et al. | 536/23.1 |

FOREIGN PATENT DOCUMENTS

| | | |
|---|---|---|
| 0410806A1 | 1/1991 | European Pat. Off. |
| 0453197A1 | 10/1991 | European Pat. Off. |
| 2074340A | 10/1981 | United Kingdom |
| WO93/06482 | 1/1993 | WIPO |

OTHER PUBLICATIONS

Brooker, et al., J. Am. Chem. Soc 64, 199 (1942).
Tijssen, et al., Biochim. Biophys. ACTA 721, 394 (1982).
Allan, et al., Can J. Microbiol. 26, 912 (1980).
Haugland, Molecular Probes Handbook of Fluorescent Probes and Research Reagents (1992-94) Set 31.
Marson, Tetrahedron., 48, 3659 (1992).
Rye, et al., Nucleic Acid Res., 20, 2803 (1992).
Rye, et al., Chem. Abstracts 117(13):127607t.
Kudinova, et al., Chemical Abstracts 93:241180j (1993).
Kudinova, et al. KHIM. Geterotsikl. Soedin. 7,903 (1980).
Simbera, et al., Chemical Abstracts 89:112299y (1978).
Nucleic Acids Research, vol. 20, No. 11, (Rye et al) pp. 2803-2812.

*Primary Examiner*—Michael G. Wityshyn
*Assistant Examiner*—Louise N. Leary
*Attorney, Agent, or Firm*—Allegra J. Helfenstein; Anton E. Skaugset

[57] ABSTRACT

The invention relates to a method of forming distinctive intravacuolar structures that are unique to fungal cells and can be correlated with cell viability. The preferred dyes of the present invention are described by the formula:

wherein
each $R^1$ is independently H; or an alkyl group having from 1-6 carbons; or a trifluoromethyl; or a halogen; or $-OR^6$, $-SR^6$ or $-(NR^6R^7)$ where $R^6$ and $R^7$, which can be the same or different, are independently H; or alkyl groups having 1-6 carbons; or 1-2 alicyclic, heteroalicyclic, aromatic or heteroaromatic rings, containing 1-4 heteroatoms, wherein the heteroatoms are O, N or S; or $R^6$ and $R^7$ taken in combination are $-(CH_2)_2-M-(CH_2)_2-$ where M = a single bond, $-O-$, $-CH_2-$, or $-NR^8-$ where $R^8$ is H or an alkyl having 1-6 carbons; and t = 1-4;

$R^2$ is an alkyl group having 1-6 carbons;

X is O, S, Se or $NR^9$, where $R^9$ is H or an alkyl group having 1-6 carbons; or X is $CR^{10}R^{11}$ where $R^{10}$ and $R^{11}$, which may be the same or different, are independently alkyl groups having 1-6 carbons, or $R^{10}$ and $R^{11}$ taken in combination complete a five or six membered saturated ring;

$R^3$, $R^4$ and $R^5$, which may be the same or different, are independently H; or an alkyl, alkenyl, polyalkenyl, alkynyl or polyalkynyl group having 1-6 carbons; or a halogen; or $-OH$, $-OR^6$, $-SR^6$ or $-(NR^6R^7)$; or $R^4$ and $R^5$, taken in combination form a quinolinium ring system that is optionally similarly substituted or unsubstituted;

$Z^-$ is a biologically compatible counterion;

L is a halogen or good leaving group; and

OMEGA is a saturated or unsaturated, substituted or unsubstituted, cyclic substituent.

35 Claims, 6 Drawing Sheets

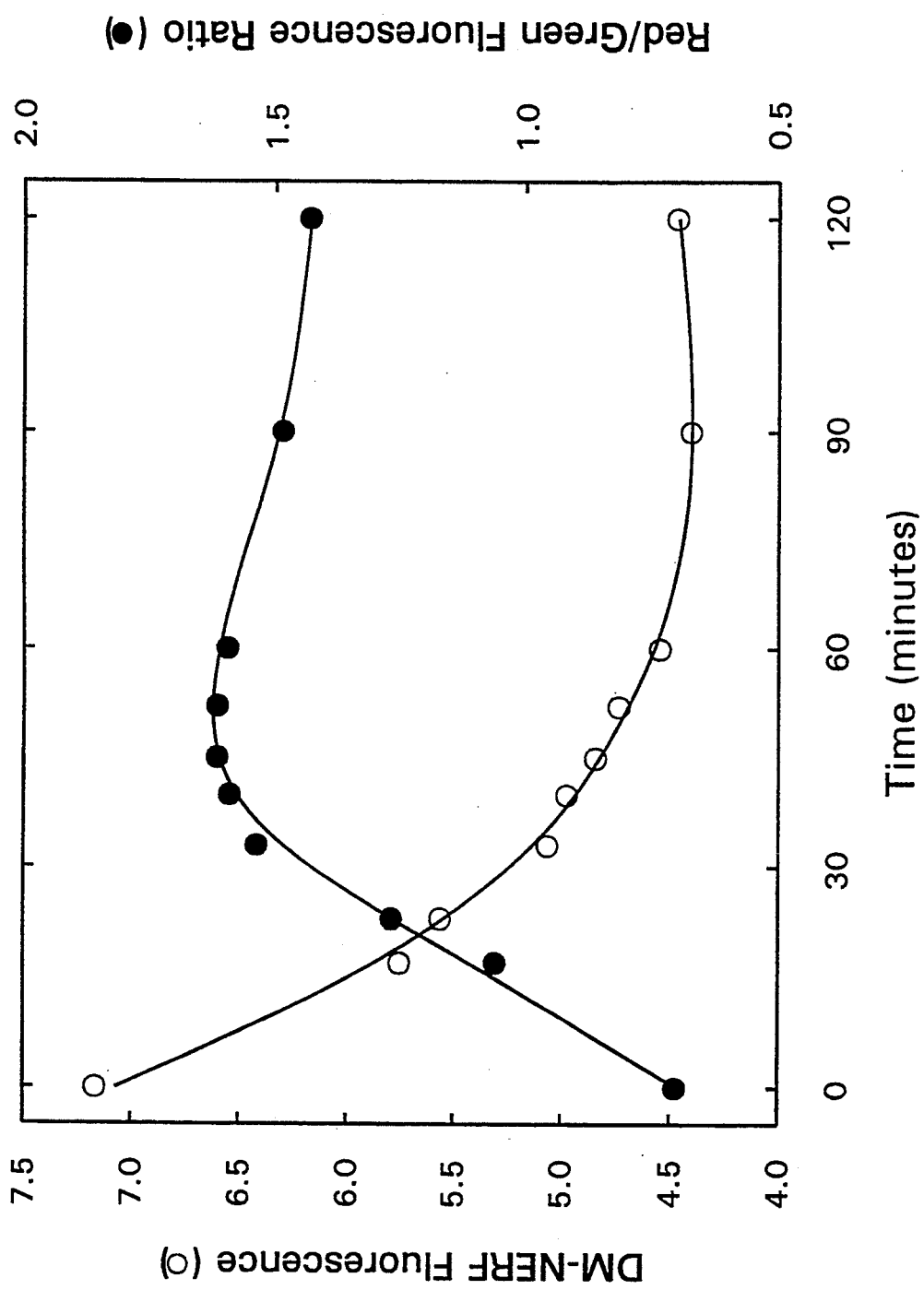

INTRAVACUOLAR STAINS FOR YEAST AND OTHER FUNGI

This application is a continuation-in-part of Ser. No. 08/090,890, filed Jul. 12, 1993, which is in turn a continuation-in-part of Ser. No. 08/047,683, filed Apr. 13, 1993 now abandoned.

FIELD OF THE INVENTION

The invention relates to unsymmetrical cyanine dyes that stain yeast and other fungi. In particular, the invention relates to cyclic substituent-containing unsymmetrical cyanine dyes that are also substituted at the 2-position by halogen or another easily displaceable substituent. The addition of these highly permeant dyes to fungal cells results in the formation of distinctive structures in the vacuoles of those cells that are actively metabolizing. This phenomenon allows the dyes to be used to investigate vacuoles, detect fungal cells, to determine the effect of metabolic enhancers or inhibitors, and to differentiate viable and non-viable fungal cells.

BACKGROUND OF THE INVENTION

Fluorescent dyes are known to be particularly suitable for biological applications in which a highly sensitive detection reagent is desirable. By binding to a specific component of a cell, a fluorescent dye can be used to detect the presence of that component in the cell and to distinguish cells containing the component. The presence of specific components in a cell can be indicative of certain conditions in the cell.

A family of highly permeant nucleic acid stains was described in the copending parent application CYCLIC-SUBSTITUTED UNSYMMETRICAL CYANINE DYES, Ser. No. 08/090,890 filed Jul. 12, 1993 by Haugland, et al. (incorporated by reference). These fluorescent dyes are similar to the compounds first described Brooker, et al., J. AM. CHEM. SOC. 64, 199 (1942) and lower alkyl (1-6) substituted unsymmetrical cyanine dyes exemplified by Thiazole Orange, as disclosed in U.S. Pat. Nos. 4,883,867 (1989) and 4,957,870 (1990) to Lee, et al. (both incorporated by reference), except that the cyclic-substituted compounds were found to stain the nucleic acids of viable and non-viable bacteria, plant and animal cells more quickly and completely.

A subset of these highly permeant stains was unexpectedly found to cause the formation of distinctive oblong or spherical structures in the vacuoles of fungi, particularly in the vacuoles of yeasts. Formation of these structures in the vacuoles does not appear to be related to nucleic acid staining and has not been described as occurring in other cells. Thus, although these dyes stain the nucleic acids of a wide variety of cells, they only induce the formation of the distinctive intravacuolar structures in fungi, particularly in yeast. The dyes that possess this property are substituted at the 2-position by halogen or other suitable functional groups that can be displaced by nucleophiles. A similarly 2-substituted derivative of Thiazole Orange does not produce these structures, nor do other cyclic-substituted dyes without these specific substituents at the 2-position (even if appropriately substituted at other positions). The dyes of the present invention induce the formation of distinctive structures in metabolically active cells but not in dead cells, making the dyes useful in determining the viability of yeast microorganisms and other fungi.

The dyes of this invention have particular advantages over other dyes that are used to distinguish viable yeast cells. Because the dyes of this invention can also be used to detect bacteria (but without the formation of the distinctive intravacuolar structures), a sample can be screened for viable yeast and contaminating bacteria at the same time. In addition, because the structures are typically fluorescent, their optical properties can be used to automate the detection and counting of cells containing such structures. This is not the case for the colored dye methylene blue, which is the most common dye used to determine yeast viability. Methylene blue staining relies on the reduction of the dye to a colorless form inside the live cell to differentiate living from non-living yeast cells. This mechanism often leads to ambiguous results as the oxidation-reduction potential varies between cells. Furthermore, the evaluation of viable yeast cells is hampered by a high background color, the difficulty in discriminating between similar shades of blue, and the presence of "false deads" in the sample (living yeast cells that nevertheless remain colored when stained with methylene blue).

Fluorescent thioflavin compounds are disclosed in U.S. Pat. No. 4,554,546 (to Wang, et al. 1985) for staining a wide range of nucleic acids, including the nucleic acids of yeast and fungi. These compounds and similar nucleic acid stains disclosed in U.S. Pat. No. 5,057,413 (to Terstappen et al. 1991) and in U.S. Patent No. 4,937,198 (to Lee et at. 1990) differ front the core chemical structure of the compounds used for Applicants' invention and do not contain an appropriate functional group susceptible to nucleophilic displacement. In addition, the thioflavin compounds do not form structures that allow the discrimination between metabolically active and inactive cells.

Fluorescent bodies in the vacuoles of yeast stained with DAPI have been reported, e.g. Tijssen, et al., BIOCHIM. BIOPHYS. ACTA 721, 394 (1982); Allan, et al., CAN. J. MICROBIOL. 26, 912 (1980) but the authors do not correlate the appearance of these bodies with yeast viability, and these dyes also do not possess a functional group susceptible to nucleophilic displacement. Furthermore, although DAPI dyes have high fluorescent enhancements, they require UV excitation and emit a blue fluorescence, making them more difficult to detect over the background cellular autofluorescence.

There is presently no fungal viability stain that combines all of the desirable properties of the present invention. The dyes of the present invention give highly fluorescent staining at wavelengths where cellular autofluorescence is relatively low, with very low background signal, easy interpretation of staining results, and good correlation with cell metabolism. In addition, the dyes of the present invention allow the simultaneous detection of bacterial contamination in a sample containing fungi, as they stain all bacteria indiscriminately.

Figure 2:
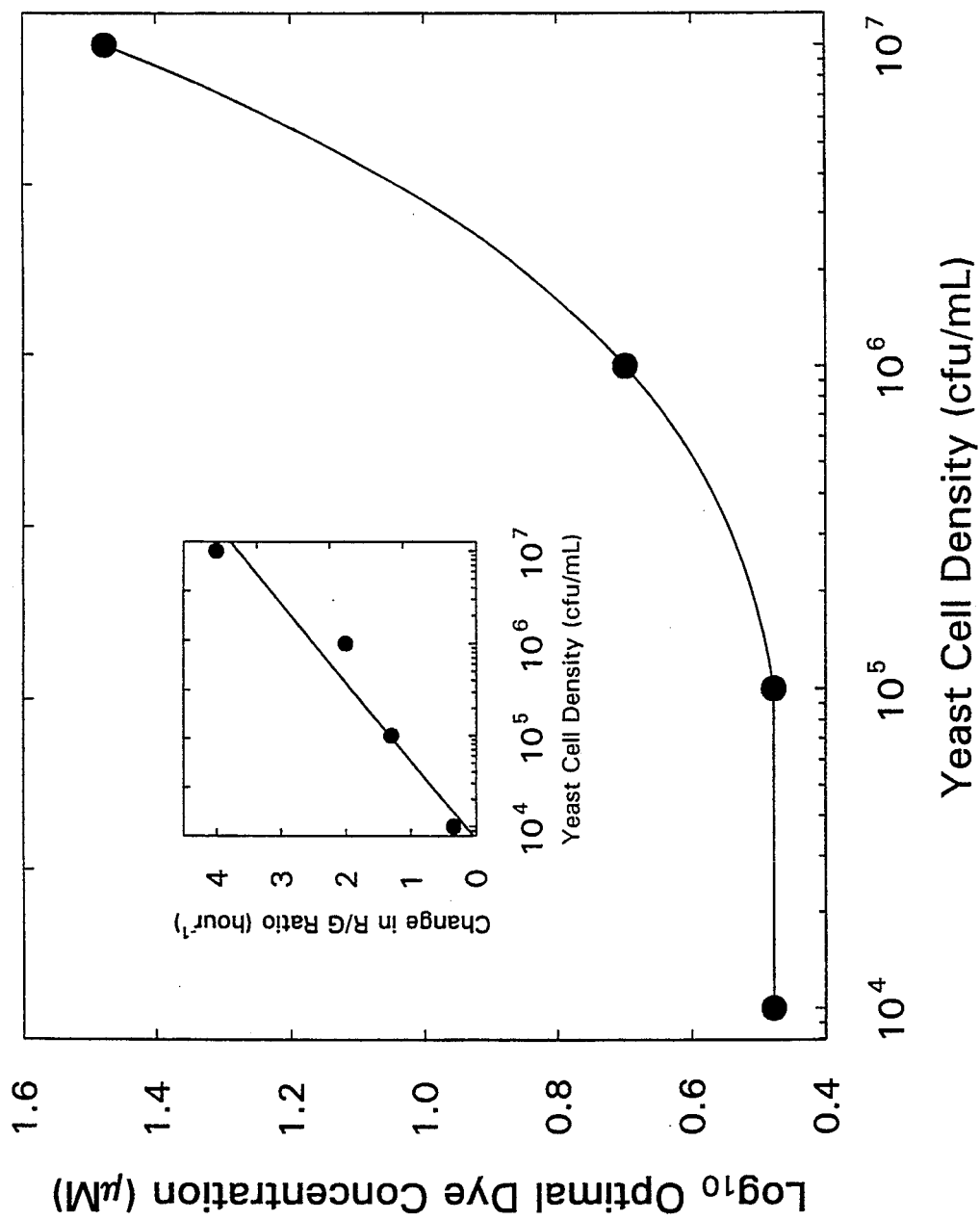

FIG. 2: The relationship between dye concentration and yeast cell density for optimal staining of Saccharomyces yeast stained with Dye 591, as determined by the procedure described in Example 8. Inset represents development of DIS fluorescence at optimal concentrations of Dye 591.

Figure 3:
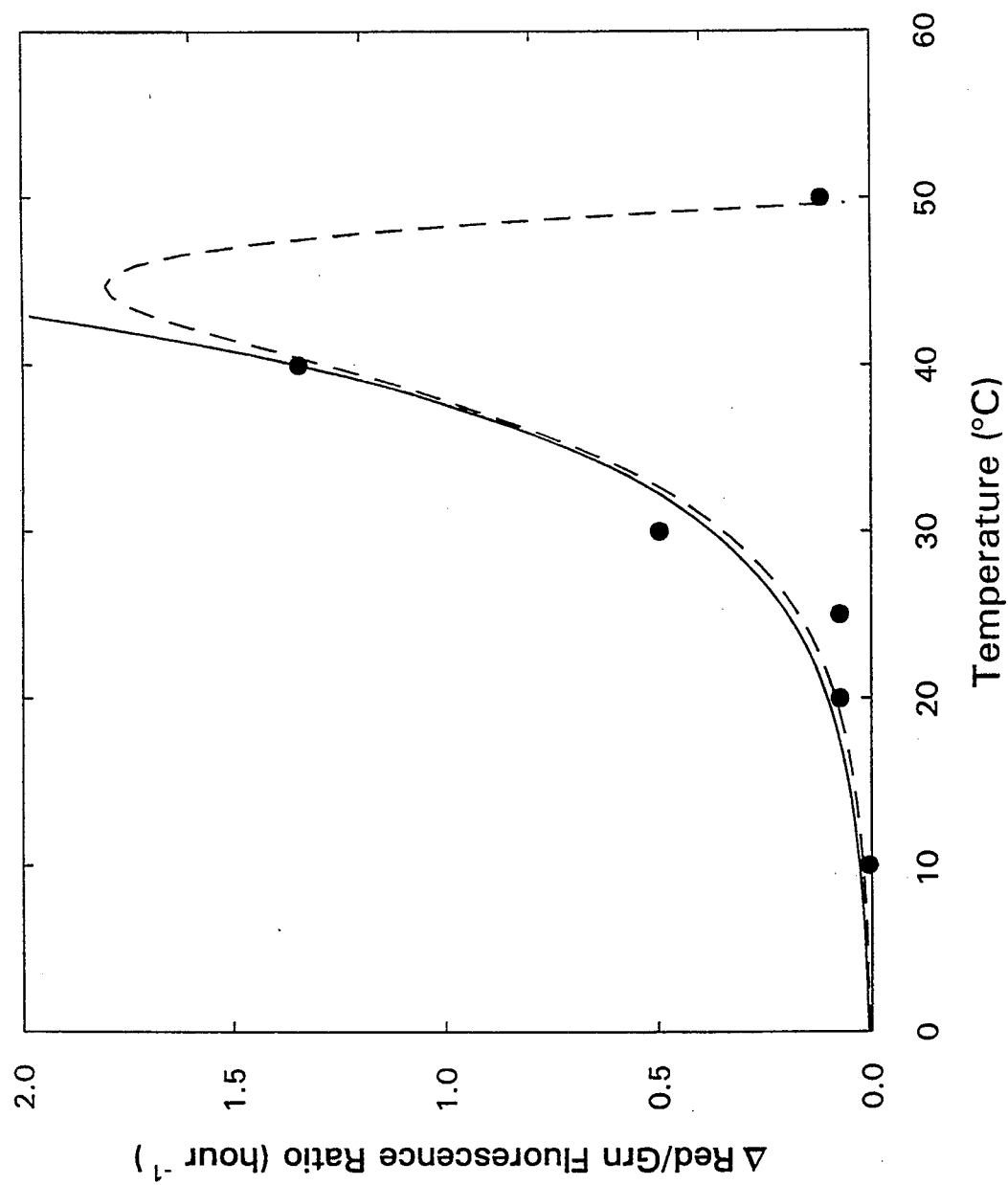

FIG. 3: The effect of temperature on the rate of formation of DIS using Dye 591 (determined by the change in red/green fluorescence ratio using the procedure described in Example 9). The solid line represents a best-fit of the exponentially increasing segment of the plot to the equation $Y=Ce^{(KX)}$, where $C=0.0020$ and $K=0.1281$. The dashed line represents the actual cellular response as fit to the equation $Y=A\sin(Be^{(CX)})$, where $A=0.4500$, $B=0.0028$ and $C=0.1411$.

Figure 4:
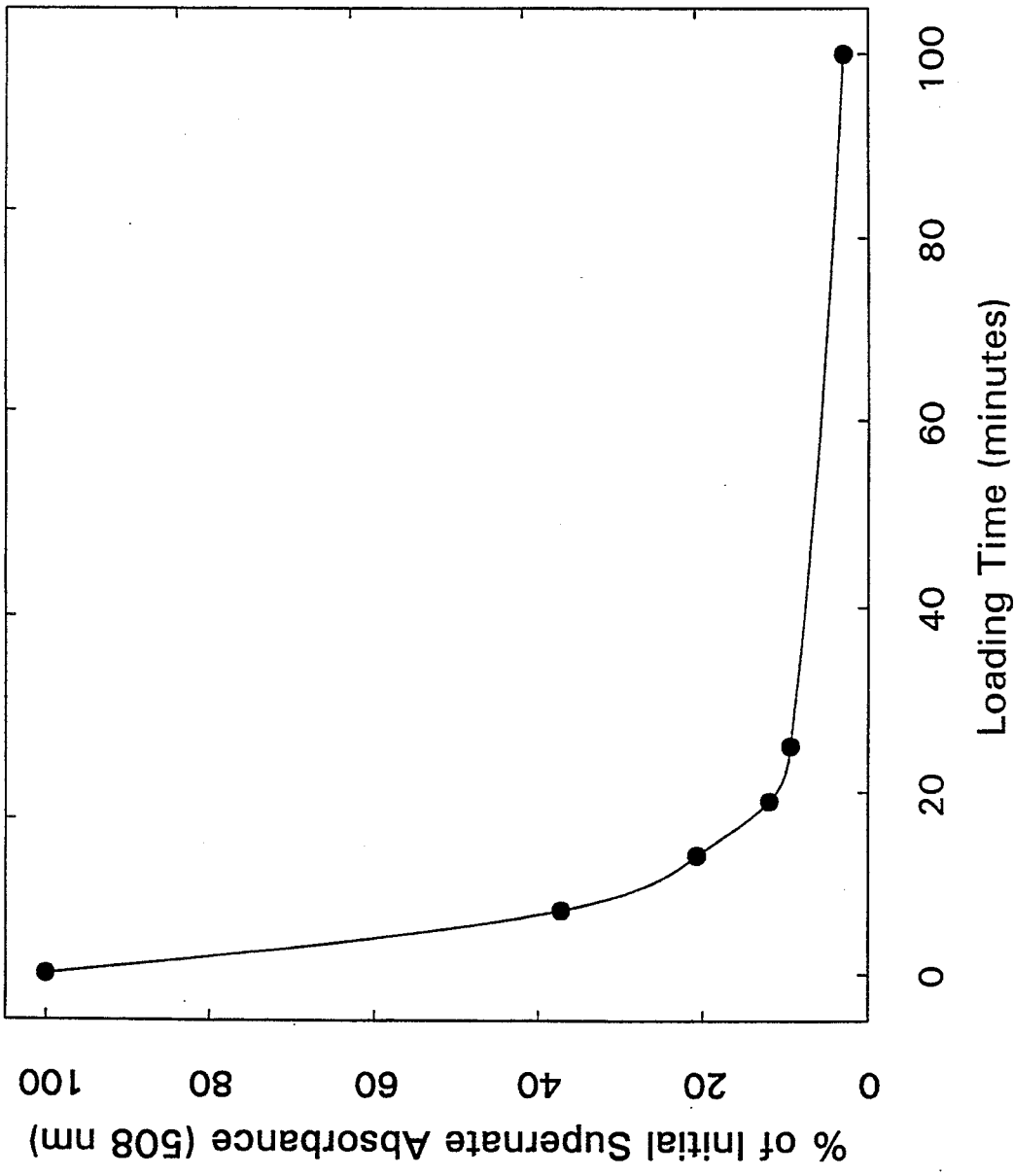

FIG. 4: The ability of yeast cells to absorb a dye of the present invention from a staining solution is depicted graphically as a function of loading time. This properly is utilized in the pulse loading of *Neurospora crassa* described in Example 10).

Figure 5:
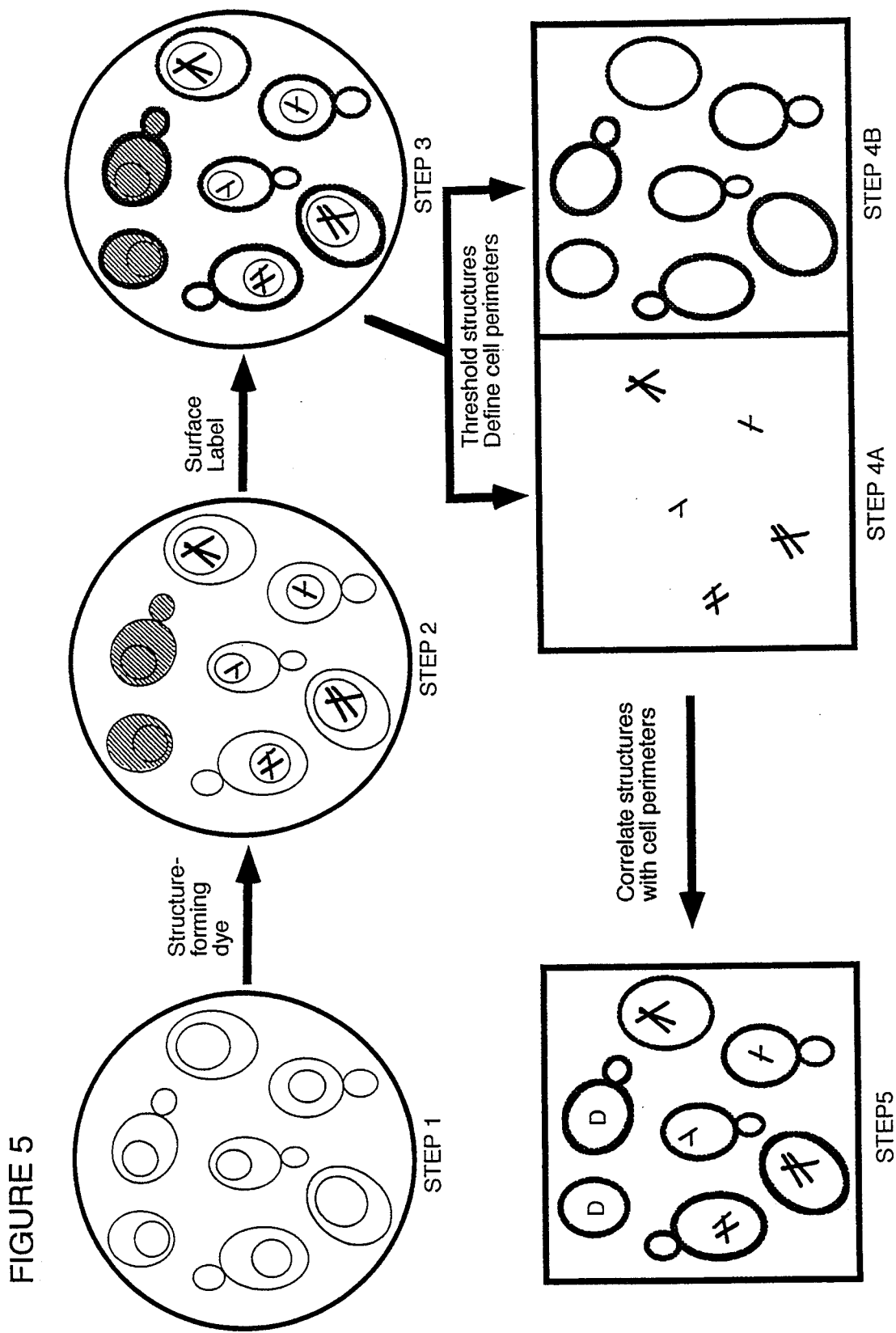

FIG. 5: The use of the dyes of the present invention to electronically son and count viable and non-viable fungi using imaging of fluorescence emission. A sample of fungi (Step 1) is stained with a dye of the present invention. Dead cells exhibit overall fluorescent staining, while viable cells exhibit formation of DIS that possess red-shifted fluorescence (Step 2). The sample is treated with a fluorescent surface label that targets both the dead and viable cell membranes (Step 3). The fluorescence emission of the sample is recorded and digitally separated into wavelengths corresponding to DIS emission (Step 4A) and surface label emission (Step 4B). The separate images are then recombined, and electronically sorted into cells that contain DIS and cells that do not contain DIS (Step 5). This procedure is described using Dye 591 and Calcofluor ™ White M2R in Example 11.

FIG. 6: The change in fluorescence ratio (reflecting DIS formation) at a single concentration of glucose is plotted with the concomitant drop in pH as determined by the pH indicator DM-NERF. The formation of DIS can therefore be correlated with carbohydrate utilization (Example 13).

SUMMARY OF THE INVENTION INCLUDING A DESCRIPTION OF PREFERRED EMBODIMENTS

The subject invention describes a method of staining fungi, including yeasts, in a sample. The method comprises adding a specified dye to a sample containing yeast or other fungal cells and allowing sufficient time for the formation of distinct intravacuolar dye complexes (hereafter called distinct intravacuolar structures, or DIS). The presence or magnitude of the DIS is optionally used as a tool for evaluating certain characteristics of the cells (or their vacuoles) in the sample.

Dyes

The dyes that are effective in the present invention are described in copending application CYCLIC-SUBSTITUTED UNSYMMETRICAL CYANINE DYES, Ser. No. 08/090,890 by Haugland et al., supra. The effective dyes are unsymmetrical cyanine dyes that are substituted by a cyclic substituent, and also substituted adjacent to the pyridinium nitrogen by a halogen or suitable leaving group. Preferred dyes of the present invention are described by the following formula:

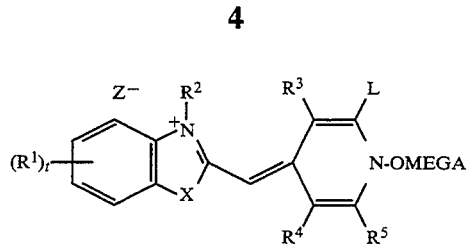

The substituent $R^1$ is typically H. The incorporation of a non-hydrogen $R^1$ can be used to fine tune the absorption and emission spectrum of the resulting dye. The benzazolium ring may contain more than one substituent $R^1$, which may be the same or different ($t=1-4$). Each $R^1$ is optionally an alkyl group having from 1-6 carbons; or a trifluoromethyl; or a halogen; or $-OR^6$, $-SR^6$ or $-(NR^6R^7)$ where $R^6$ and $R^7$, which can be the same or different, are independently H; or alkyl groups having 1-6 carbons; or 1-2 alicyclic, heteroalicyclic, aromatic or heteroaromatic rings, containing 1-4 heteroatoms (wherein the heteroatoms are O, N or S); or $R^6$ and $R^7$ taken in combination are $-(CH_2)_2-M-(CH_2)_2-$ where M is a single bond, $-O-$, $-CH_2-$, or $-NR^8-$ where $R^8$ is H or an alkyl group having 1-6 carbons. Typically, the compound contains no more than one $R^1$ that is not H.

The substituent $R^2$ is an alkyl group having 1-6 carbons, preferably methyl or ethyl, more preferably methyl.

X is O, S, Se or $NR^9$, where $R^9$ is H or an alkyl group having 14 carbons. Preferably X is O or S. Alternatively X is $CR^{10}R^{11}$ where $R^{10}$ and $R^{11}$, which may be the same or different, are independently alkyl groups having 1-6 carbons, or $R^{10}$ and $R^{11}$ taken in combination complete a five or six membered saturated ring. Typically, $R^{10}$ and $R^{11}$ are each methyl.

The substituents on the second ring system, $R^3$, $R^4$ and $R^5$, may be the same or different, and are independently H; or an alkyl, alkenyl, polyalkenyl, alkynyl or polyalkynyl group having 1-6 carbons; or a halogen; or $-OH$, $-OR^6$, $-SR^6$ or $-(NR^6R^7)$, as defined previously; or $R^4$ and $R^5$, taken in combination, form a fused 6 membered aromatic ring. Where $R^4$ and $R^5$ form a fused 6 membered aromatic ring, the dyes of this invention are 4-quinolinium derivatives according to the formula:

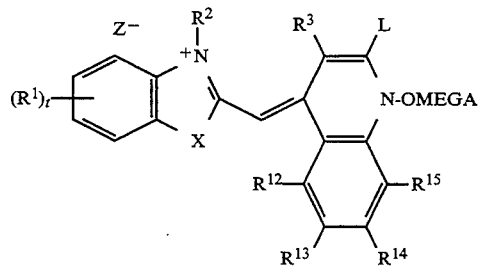

The ring substituents $R^{12}$, $R^{13}$, $R^{14}$ and $R^{15}$, which may be the same or different, are independently H; or an alkyl, alkenyl, polyalkenyl, alkynyl or polyalkynyl group having 1-6 carbons; or a halogen; or $-OH$, $-OR^6$, $-SR^6$ or $-(NR^6R^7)$ as defined previously. Preferably $R^{12}$, $R^{13}$, $R^{14}$, $R^{15}$, and $R^3$ (as well as $R^4$ and $R^5$ when the second ring system is a pyridinium) are independently H, alkyl or alkoxy. Typically no more than one of $R^{12}$, $R^{13}$, $R^{14}$, $R^{15}$, and $R^3$ (as well as $R^4$ and $R^5$ when the second ring system is a pyridinium) is not H; more typically all are H.

The counterion $Z^-$ is a biologically compatible ion that is stable and synthetically accessible. As used herein, a substance that is biologically compatible is not toxic as used, and does not have a substantially deleterious effect on biomolecules. Examples of $Z^-$ include, among others, chloride, bromide, iodide, sulfate, alkanesulfonate, arylsulfonate, phosphate, perchlorate, tetrafluoroborate, tetraphenylboride, nitrate and anions of aromatic or aliphatic carboxylic acids. Preferred $Z^-$ counterions are chloride, iodide, perchlorate and various sulfonates.

The ring substituent L is Cl, Br, I, F, or $-OSO_2R^{16}$ where $R^{16}$ is alkyl having 1–6 carbons or perfluoroalkyl having 1–6 carbons or aryl. Typically L is Cl, Br, or I. Preferably L is Cl.

OMEGA is a saturated or unsaturated, substituted or unsubstituted, cyclic substituent that has a total of 2–16 ring carbon atoms in 1–2 alicyclic, heteroalicyclic, aromatic, or heteroaromatic rings, containing 1–4 heteroatoms (wherein the heteroatoms are O, N or S). The cyclic substituent is unsubstituted or optionally substituted one or more times, independently, by halogen, alkyl, perfluoroalkyl, amino, alkylamino, dialkylamino, alkoxy or carboxyalkyl, having 1–6 carbons. Typically OMEGA is a substituted or unsubstituted cyclohexyl, cyclohexenyl, morpholino, piperidinyl, naphthyl, phenyl, thienyl, benzothiazolyl, furanyl, oxazolyl, benzoxazolyl, or pyridinyl. Preferably OMEGA is a substituted or unsubstituted naphthyl, phenyl, thienyl, morpholino, or cyclohexyl, more preferably phenyl or cyclohexyl.

Preparation of Staining Solution

Typically, the dye is added to the sample in a staining solution, which is prepared by dissolving the dye directly in an aqueous solvent that is biologically compatible with the sample, such as water or tissue culture medium or buffer such as HEPES buffered saline, or in an organic water-miscible solvent such as dimethylsulfoxide (DMSO), dimethylformamide (DE, or a lower alcohol such as methanol or ethanol, or acetonitrile. Preferably the staining solution is completely used within one day and a new staining solution is subsequently prepared. Typically the dye is preliminarily dissolved in an organic solvent (preferably DMSO) at a concentration of greater than about 100-times that used in the staining solution and then diluted one or more times with an aqueous solvent such as water or buffer, such that the dye is present in an effective amount. An effective amount of dye is the amount sufficient to give one or more distinct intravacuolar structures (DIS) when combined with viable yeast.

The amount of dye needed to form DIS depends on the type and amount of cells in the sample, the type of sample, as well as the dye itself. Typically a stock solution of dissolved dye is diluted in water to about 120 $\mu M$, then further diluted to a final concentration in the staining solution to greater than about 1 $\mu M$, depending on the cell density as described below. For a cell density of $10^5$–$10^8$ cells/mL, preferably the final concentration of dye in the staining solution is between about 1 $\mu M$ and 100 $\mu M$, more preferably between 1 $\mu M$ and 50 $\mu M$.

The rate of formation of DIS, as well as the size of the DIS formed, is dependent upon the concentration of sample cells, the concentration of dye in the staining solution, and the temperature of the sample. A sample containing $10^6$ cells will exhibit slower formation of DIS, and smaller structures, than a sample containing $10^4$ cells at the same dye concentration. It is therefore possible to achieve satisfactory staining and viability assessment of yeast cells at concentrations of dye less than 1 $\mu M$, if the sample size is equivalently reduced.

At high concentrations of dye (typically greater than about 30 $\mu M$) cell division and growth of the cells is permanently inhibited. At lower concentrations of dye (typically between 1 and 5 $\mu M$) growth and cell division is inhibited, but upon removing the cells from the staining solution, growth and cell division resume.

The staining solution optionally contains additional dyes, growth factors, buffers, or chelators and preferably does not contain extracellular nucleic acids that may result in background staining. Reagents or conditions that temporarily enhance the permeability of materials into cells such as hypotonic medium or detergents may be present, but are usually not necessary. Typically the staining solution contains a physiological buffer such as HEPES (Gibco).

The Sample

The sample contains, or is thought to contain, one or more fungal cells or varieties of fungal cells, where the cells contain one or more vacuoles. Typically, the fungal cells are yeast cells. The fungal cells may be of interest for commercial reasons, as a pathogenic species, or as an experimental model (e.g. Saccharomyces, Candida, Neurospora). The sample can be obtained from a wide range of sources. In one aspect of the invention, the sample is taken directly from a fermentation process, such as the process of making fermented beverages, food products, vitamins or drugs, or contains a fermentation yeast such as Saccharomyces. In another embodiment of the invention, the sample contains cultured yeast, for example from a research facility or medical laboratory. The sample fungal cells can be a mutant strain, or contain cloned or altered genetic material. The sample optionally contains additional contaminants or other non-fungal cells, such as bacteria or cells of higher eukaryotes.

The cells in the sample are optionally in suspension or are located on a solid or semisolid support. In one embodiment of the invention, the sample is in suspension on a microscope slide or in a specialized container required for a specific instrumentation detection method, such as in a cuvette or in a microtiter plate (e.g. 96 well titer plate). Alternatively, the cells in the sample are attached to a filter as a retained residue.

Staining the Sample

The staining solution is combined with a sample containing the cells of interest. Depending on the type of sample and characteristics of the cell population thought to be contained in the sample, the sample is added to the staining solution or the staining solution is added to the sample. For example, a filter containing a residue removed from a liquid sample can be placed in the aqueous dye solution, allowing the residue to incubate in the dye solution. Alternatively, where the sample is placed on a slide or in a specialized container, the staining solution can be added to the slide or container before or after the addition of the sample.

After the staining solution is combined with a sample, sufficient time is allowed for the dye in the solution to stain cells in the sample so that formation of distinct intravacuolar structures (DIS) can be evaluated. Typically, more than about 10 or 15 minutes is sufficient time for the dye to stain cells in the sample. More typically, the dye solution is combined with the sample for more than about 30 minutes. Practically instantaneous generation of DIS is achieved when a metabolizable carbohydrate is added to cells for which the metabolism is previously suppressed. The cells are treated overnight with a non-metabolizable substrate (e.g. 2% 2-deoxyglucose containing 0.5% sodium azide). After washing the cells free of the substrate, the cells are stained with the subject dyes. Very few if any DIS appear even after an hour of incubation, but appear virtually instantaneously when a metabolizable carbohydrate (e.g. 2% glucose and 10 mM HEPES) is added to the cell medium.

Metabolic Effector

One aspect of the invention utilizes a metabolic effector, which is a change in environmental condition or a material that affects the metabolic activity of the cell, or the ability of the cell to grow or reproduce, including exposure to a chemical reagent, the addition of a biological agent, or other physical change. The metabolic effector may enhance or inhibit the metabolic activity of the cells (even to the extent of causing cell death). Many chemical reagents are known to be metabolic effectors, including organic solvents, surfactants, toxins, ionophores, drugs, mitochondrial inhibitors (including uncouplers), acids and bases, chaotropic ions, enzyme inhibitors, oxidizing and reducing agents, etc. Typically chemical reagents are cytotoxic. Biological agents known to be metabolic effectors include cytotoxic cells, neutrophils, macrophages, complement, some lectins, antibiotics, toxins, metabolizable carbohydrates (such as glucose and other mono-, oligo- and polysaccharides), drugs, enzymes, metabolites, cofactors, exogenous nucleic acids (such as vectors and DNA coding for selected proteins), and others. Environmental conditions known to be metabolic effectors include hyperthermia, hypothermia, freezing, ionizing radiation, light, hypoosmotic and hyperosmotic shock, compression, decompression, rate of mixing, physical disruption, and others. The sample may be exposed to the metabolic effector before, after or concurrently with the addition of the mining solution.

For example, the size and number of structures is noticeably enhanced in the presence of a metabolizable carbohydrate. A metabolizable carbohydrate is a carbohydrate that can be taken up by the cells in the sample for use as an energy source (e.g. glucose and other sugars). In a preferred embodiment of the invention, the stained yeast sample contains an amount of metabolizable carbohydrate sufficient to activate cell metabolism, typically from about 1% to about 25% carbohydrate (weight/volume). More preferably the stained sample contains about 5% carbohydrate (weight/volume). The carbohydrate is optionally added after the sample is stained, or is present in the sample in sufficiently high concentration to give a concentration of about 1% to about 25% in the stained sample after addition of the staining solution.

Additional Detection Reagent

The use of the dyes of the present invention in fungal cells is optionally combined with the use of an additional detection reagent. An additional detection reagent is a reagent that produces a detectable response in the fungal cell or cells due to the presence of a specific cell component, intracellular substance, or cellular condition. The additional detection reagent is optionally a fluorophore, luminophore, radioactive isotope, free radical, enzyme, coenzyme, hapten, protein, nucleic acid, microparticle, liposome, metal, chelate, magnetic material, electrophore, electrochemiphore, chromophore, a labeled specific binding pair member, or any other reagent that produces a detectable response. A detectable response is a change in, or occurrence of, a parameter in a test system which is capable of being perceived, either by direct observation or instrumentally. In one aspect of the invention, the additional detection reagent is used to differentiate live cells from dead cells, for example by indicating whether the integrity of the cell membrane is intact or disrupted. Alternatively, the additional detection reagent is utilized to detect or analyze some intracellular process such as by detecting the presence of a protein or genetic code or metabolic indicator. In yet another aspect of the invention, the additional detection reagent is used to identify or classify the type of fungal cell, for example by the presence of some surface or intracellular characteristics. Multiple parameters may be evaluated by use of one or more additional detection reagents. The additional detection reagent is added either prior or simultaneously with or subsequent to addition of the subject dye to the sample. The concentration of the additional detection reagent and incubation time is typically adjusted so as not to obscure the staining with the subject dyes.

In one aspect of the invention, a fluorescent nucleic acid stain is used as an additional detection reagent. A variety of appropriate nucleic acid stains are known in the art, (see, e.g. Haugland, MOLECULAR PROBES HANDBOOK OF FLUORESCENT PROBES AND RESEARCH REAGENTS (1992-94) Set 31 incorporated by reference) including but not limited to, Thiazole Orange, ethidium homodimer, propidium iodide, aminoactinomycin, Hoechst 33258, and DAPI. The use of an appropriate nucleic acid stain in conjunction with the dyes of the present invention can be selected to allow simultaneous observation of mitochondria, nuclear DNA, RNA and/or mitochondrial DNA.

Additional nucleic acid stains that are impermeant with respect to intact cellular membranes are described in Haugland, supra, and copending applications DIMERS OF UNSYMMETRICAL CYANINE DYES (by Haugland et at, Ser. No. 07/761,177, filed Sep. 16, 1991, now abandoned, published as PCT international publication no. WO 93/06482), UNSYMMETRICAL CYANINE DYES WITH CATIONIC SIDE CHAIN (by Yue et al, Ser. No. 07/833,006, filed Feb. 8, 1992, now U.S. Pat. No. 5,321,130), or DIMERS OF UNSYMMETRICAL CYANINE DYES CONTAINING PYRIDINIUM MOIETIES (by Yue et al., Ser. No. 08/043,665, filed Apr. 5, 1993, now U.S. Pat. No. 5,410,030) (all three patent applications incorporated by reference). These dyes have been found useful for probing membrane integrity by only staining the nucleic acids present in cells that have disrupted membranes. The counterstain is preferably selected so that it possesses a spectral properties detectably different from that of the structure forming dye.

Other appropriate additional detection agents are fluorescent indicators for intracellular ions (e.g. Haugland, supra, Sets 20-22 incorporated by reference) and any of the fluorescent metal ion indicators described in copending applications REACTIVE DERIVATIVES OF BAPTA USED TO MAKE ION-SELECTIVE CHELATORS (by Kuhn, et al., copending Ser. No. 07/843,360, filed Feb. 25, 1992) or FLUORESCENT ION-SELECTIVE DIARYLDIAZA CROWN ETHER CONJUGATES Coy Kuhn et al., Ser. No. 08/039,918, filed Mar. 29, 1993, now abandoned).

In yet another aspect of the invention, a detection reagent specific for an intracellular membrane or organelle (e.g. mitochondria) is utilized, such as described in Haugland, supra, Set 30 incorporated by reference, or those described in copending application XANTHYLIUM DYES THAT ARE WELL RETAINED IN MITOCHONDRIA (copending Ser. No. 08/143,440 filed Oct. 25, 1993 by Haugland, et al)(incorporated by reference).

Alternatively, the additional detection reagent comprises: a) one member of a specific binding pair or a series of specific binding pairs, and b) means for producing a detectable response (label). A specific binding pair member can be a ligand or a receptor. As used in this document, the term ligand means any compound for which a receptor naturally exists or can be prepared. A receptor is any compound or composition capable or recognizing a spatial or polar organization of a molecule, e.g. epitopic or determinant site. Ligands for which naturally occurring receptors exist include natural and synthetic proteins, including avidin and streptavidin, antibodies, enzymes, and hormones; nucleotides and natural or synthetic oligonucleotides, including primers for RNA and single- and double-stranded DNA; lipids; polysaccharides and carbohydrates; and a variety of drugs and toxins, including therapeutic drugs and drugs of abuse and pesticides, as well as known reagents for specific receptors (e.g. Haugland, supra, Set 29 incorporated by reference). Typically the additional detection reagent is used for cell surface markers or for markers of organdies because of difficulty in permeabilizing living fungal cells without destroying or inhibiting their metabolic activity.

Ligands and receptors are complementary members of a specific binding pair, each specific binding pair member having an area on the surface or in a cavity which specifically binds to and is complementary with a particular spatial and polar organization of the other. Representative specific binding pairs are shown in Table 1.

The additional detection reagent may be used in conjunction with substrates and enzyme conjugates to localize cellular receptors; to probe for coding sequences or identify mutant or transformed cells; or to probe cells that do not express the enzyme; for example, by enzyme-linked immunosorbent assay (ELISA), or enzyme-mediated histochemistry or cytochemistry, or other enzyme-mediated techniques. Enzyme-mediated techniques take advantage of the association of specific binding pairs to detect a variety of analytes.

TABLE 1

| REPRESENTATIVE SPECIFIC BINDING PAIRS | |
| --- | --- |
| antigen | antibody |
| hapten | antibody |
| biotin | avidin (or streptavidin) |

TABLE 1-continued

| REPRESENTATIVE SPECIFIC BINDING PAIRS | |
| --- | --- |
| IgG* | protein A or protein G |
| drug receptor | drug |
| toxin receptor | toxin |
| carbohydrate | lectin |
| peptide receptor | peptide |
| protein receptor | protein |
| carbohydrate receptor | carbohydrate |
| DNA (RNA) | aDNA (aRNA) |

*IgG is an immunoglobulin
aDNA and aRNA are the antisense (complementary) strands used for hybridization In general, an enzyme-mediated technique uses an enzyme attached to one member of a specific binding pair or series of specific binding pairs as a reagent to detect the complementary member of the pair or series of pairs. In the simplest case, only the members of one specific binding pair are used. One member of the specific binding pair is the analyte, i.e. the substance of analytical interest. An enzyme is attached to the other (complementary) member of the pair, forming a complementary conjugate. Alternatively, multiple specific binding pairs may be sequentially linked to the analyte, the complementary conjugate, or to both, resulting in a series of specific binding pairs interposed between the analyte and the detectable enzyme of the complementary conjugate incorporated in the specific binding complex. Table 2 shows the representative examples of specific binding complexes with and without additional specific binding pairs interposed between the complementary conjugate and the analyte.

The additional detection reagent also incorporates a means for producing a detectable response. A detectable response means a change in, or occurrence of, a parameter in a test system that is capable of being perceived, either by direct observation or instrumentally, and which is a function of the presence of a specifically targeted member of a specific binding pair in a cell sample. Such detectable responses include the change in, or appearance of, color, fluorescence, reflectance, pH, chemiluminescence, luminescence, phosphorescence, infrared spectra, spin resonance spectra, or an electron-rich substrate. Appropriate labels to provide a detectable response include, but are not limited to, a visible or fluorescent dye, an ettzyme substrate which produces a visible or fluorescent precipitate upon enzyme action (for example, the action of horseradish peroxidase upon diaminobenzidine), visible or fluorescent labeled latex microparticles, or a signal that is released by the action of light upon the reagent (e.g. a caged fluorophore that is activated by photolysis, or the action of light upon diaminobenzidine). In preferred embodiments, the additional detection reagent is selected such that the detectable response of the additional detection reagent is perceptibly distinct from the response of the dye of the present invention.

TABLE 2

| REPRESENTATIVE SPECIFIC BINDING COMPLEXES | | | | |
| --- | --- | --- | --- | --- |
| ANALYTE | ADDITIONAL PAIRS | | | COMPLEMENTARY CONJUGATE |
| DNA | aDNA--biotin | avidin | — | biotin--enzyme |
| DNA | aDNA--antigen | antibody--biotin | avidin | biotin--enzyme |
| DNA | — | — | — | aDNA--enzyme |
| DNA | aDNA--biotin | — | — | avidin--enzyme |
| DNA | aDNA--hapten* | — | — | anti-hapten--enzyme |
| RNA | aRNA--hapten* | — | — | anti-hapten--enzyme |
| RNA | aDNA--biotin | — | — | avidin-enzyme |

TABLE 2-continued

REPRESENTATIVE SPECIFIC BINDING COMPLEXES

| ANALYTE | ADDITIONAL PAIRS | | | COMPLEMENTARY CONJUGATE |
|---|---|---|---|---|
| antigen | mouse antibody | anti-mouse--biotin | — | avidin-enzyme |
| antigen | mouse antibody | anti-mouse | mouse anti-enzyme | enzyme |
| antigen | — | — | — | antibody--enzyme |
| antigen | antibody--hapten* | — | — | anti-hapten--enzyme |
| carbohydrate | lectin--biotin | — | — | avidin--enzyme |
| receptor | ligand--biotin | — | — | anti-biotin--enzyme |
| IgG | protein A--hapten* | — | — | anti-hapten--enzyme |

*a group, typically a low molecular weight molecule such as a drug, dye, or aromatic molecule, that does not itself generate an immune response unless attached to a carrier molecule for instance a drug receptor, a toxin receptor, peptide receptor, protein receptor or carbohydrate receptor –is a covalent bond between two reagents; all other bonds are noncovalent Distinct Intravacuolar Structures After sufficient time has elapsed, a stained cell that is metabolically active will display the formation of one or more distinctive intravacuolar structures. The DIS comprise one or more oblong or rounded shapes present in the vacuole. The characteristic morphology of the DIS allow them to be detected using any instrumentation that utilizes transmitted light, including but not limited to fluorescence, polarized and nonpolarized light, and brightfield illumination. Typically, the DIS is highly fluorescent, i.e. emitting light in a fluorescent manner when illuminated with light of an appropriate wavelength. The fluorescence properties of representative dyes of the present invention are shown in Table 3.

can be identified hours, days, or even weeks after staining with the dyes of the present invention.

The staining pattern of the dyes is distinctive to fungal cells, and have not been observed in either bacteria or higher eukaryotic cells that were tested. The staining pattern, or DIS, displays significant fluorescence enhancement. Fluorescent enhancement refers to the increase in fluorescence emitted by a dye complex versus the fluorescence emitted by the unbound dye in solution, when both are similarly illuminated. Although the fluorescence enhancement for the DIS is comparable to that of a dye-nucleic acid complex (typically about a 100-fold to about a 1000-fold enhancement in fluorescence over unbound dye), the emission spectra for the

TABLE 3

SPECTRAL PROPERTIES OF REPRESENTATIVE DYES

| Dye # | Excitation/Emission (nm) DNA | Excitation/Emission (nm) RNA | Fluorescence Enhancement DNA | Fluorescence Enhancement RNA | DNA affinity | Emission maximum (nM) $T_0$ | Emission maximum (nM) $T_{30}$ |
|---|---|---|---|---|---|---|---|
| 578 | 470/504 | 471/506 | 36 | 126 | $4.1 \times 10^6$ | 505 | 555 |
| 582 | 516/533 | 518/538 | 228 | 1027 | $2.9 \times 10^6$ | 538 | 575 |
| 591 | 509/532 | 517/536 | 169 | 653 | $3.8 \times 10^6$ | 535 | 580 |
| 5103 | 511/530 | 513/533 | 305 | 1715 | $3.7 \times 10^6$ | 530 | 613 |
| 616 | 474/505 | 470/504 | 161 | 91 | $3.8 \times 10^5$ | 495 | 525 |
| 633 | 490/508 | 492/513 | 150 | 626 | $7.4 \times 10^5$ | 510 | 530 |
| 774 | 517/533 | 518/538 | 185 | 650 | $7.9 \times 10^6$ | 530 | 570 |
| 780 | 513/536 | 516/543 | 24 | 422 | $3.4 \times 10^6$ | — | — |

When the sample is excited at 470 nm $T_0$ represents the initial fluorescent staining of Saccharomyces. $T_{30}$ represents fluorescent staining of Saccharomyces after 30 minutes.

The DIS is small enough to display mobility within the vacuole, or alternatively is large enough that it is relatively immobilized by the vacuolar membrane. The DIS is optionally a single sausage-like cylinder, or spherical structure, or the DIS complex contains multiple cylinders or spheres that form parallel to each other or in a cross or starburst shape. Typically, when the dye used possesses a cyclic substituent that is saturated, the intravacuolar structures that are formed are generally spheres to short cylinders. In contrast, when the dye used possesses a cyclic substituent that is unsaturated, the intravacuolar structures that form are generally cylindrical.

Figure 1:
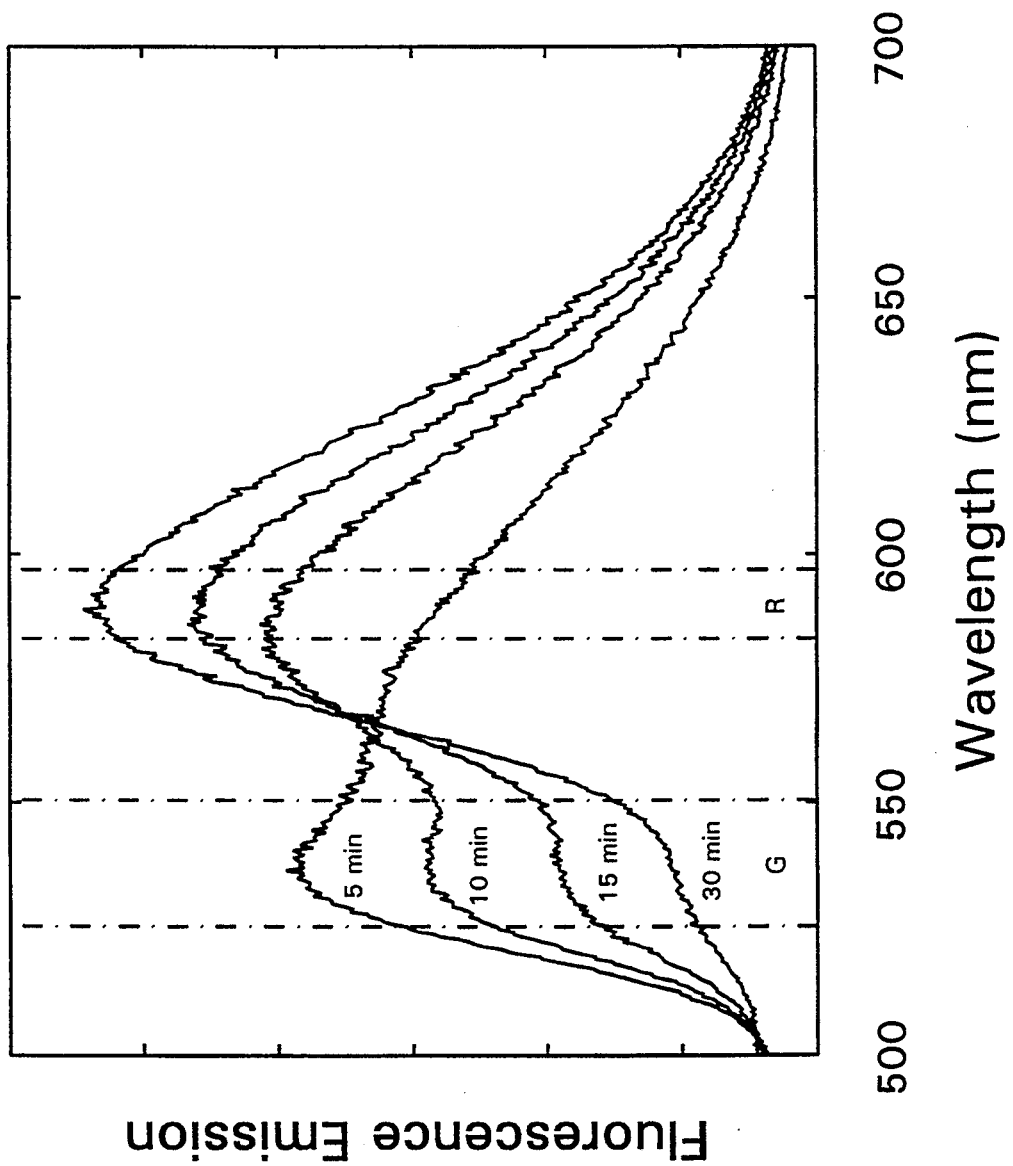
FIG. 1: The shift from green fluorescence to red fluorescence exhibited by dyes of the present invention in metabolically active yeast cell. Dye 591 is added to a suspension of *Saccharomyces cerevisiae*, and the sample is excited at 480 nm in a fluorometer. The fluorescence emission spectrum of the sample is recorded over a 30 minute time period. The shift from green to red fluorescence reflects formation of DIS in the sample cells.

The distinctive complex forms in the vacuoles of metabolically active cells, but not in dead cells or cells where the metabolism is inactivated. Although there is no detectable growth after about 24 hours in the presence of the stain, the formation of the DIS is not necessarily toxic to the cells. After washing and transferring the cells to fresh growth media, the cells grow once again, even though the DIS complexes formed previously are still present in the vacuoles of the parent cells. Once the DIS have formed, fungal cells containing DIS DIS are distinctively different. In particular, formation of the DIS results in a bathochromic shift relative to the emission spectrum for the same dye complexed to nucleic acids. Typically, the emission maximum of the DIS occurs at a wavelength that is more than about 20 nm longer than the emission maximum of the same dye complexed to nucleic acids in solution (see Table 3). For example, the monomethine dyes of the present invention typically yield a green fluorescence in combination with cell-free nucleic acids and a bright yellow-green stain throughout dead fungal cells. These same dyes, however, induce distinctive fluorescent structures in the vacuoles of live cells that are typically bright red, orange, yellow or green (see FIGS. 1 and 5). As DIS are formed in metabolically active cells, the fluorescence emission of the sample undergoes a shift from green fluorescence to red fluorescence.

The staining pattern typically procedes through a series of phases, as shown in Table 4 below. While the specific DIS colors listed below are representative of Compound 591, the staining pattern is essentially independent of the substituents on the dyes except, as mentioned previously, where the overall morphology of the DIS is different for saturated versus unsaturated cyclic substituents on the dye.

The staining of yeast cells that are dead and possess disrupted cellular membranes is also distinctive. Upon staining with a dye of the present invention, a dead cell will display rapid overall staining, with no differentiation. Staining of a mixed sample containing both live and dead yeast cells will result in the formation of DIS in living, metabolizing cells, and much brighter overall staining in dead cells. Live and dead cells can then readily be identified and analysed, either qualitatively or quantitatively.

TABLE 4

REPRESENTATIVE STAINING PROGRESSION

| time | appearance |
| --- | --- |
| 0 to 5 minutes | Whole yeast, except vacuole, turns green to yellow-green fluorescent |
| 5–10 minutes | Nuclear region turns brighter green or yellow-green fluorescent than the cytoplasm. The vacuole has diffuse weak orange fluorescence. A few punctate green fluorescent and punctate orange to red fluorescent spots form in the cytoplasm. |
| 10–15 minutes | Nuclear staining is completely lost. Cytoplasmic staining becomes weaker. Some punctate green spots remain in the cytoplasm, but the punctate red spots are gone. Background fluorescence in the vacuole is lost, but orange to red fluorescent DIS develop in the vacuole. These grow and show extensive Brownian motion. |
| 15–30 minutes | The orange to red fluorescent DIS are considerably larger and grow until they distend the vacuole and become immobile. The rest of the vacuole is essentially nonfluorescent, as is the cytoplasm. A few green fluorescent punctate spots remain in the cytoplasm. |

Non-fungal cells or sample contaminants, such as bacteria or higher eukaryotic cells, are readily observed in the stained sample. The dyes of the present invention permeate bacterial and eukaryotic cells, and stain the nucleic acids present in the cells. The fluorescence emission of the dyes bound to nucleic acids is perceptibly different than that of the DIS (as discussed earlier) allowing differentiation of non-fungal cells from the fungal cells. Some non-fungal cells are also readily identified or distinguished by their size and morphology.

Evaluation

Once sufficient time has elapsed for staining the intracellular nucleic acids in the sample, the sample is prepared for evaluation. The type of preparation depends on the type of sample and the method of detection being utilized. In one aspect of the invention, detection is visually observing the formation of DIS in the sample cells using a microscope and brightfield illumination. It is not necessary, however, that the structures be observed or detected to evaluate their presence because the bathochromic shift in the fluorescence signal or the ratio of different fluorescent signals can be used to analyze the sample without determining whether the structures themselves are present. In another aspect of the invention, the sample is evaluated using conditions under which the DIS are fluorescent. In this aspect, the preparation of the sample generally comprises illuminating the sample at a wavelength that will excite fluorescence of the DIS. The illumination can be accomplished by any light source capable of producing light at or near the wavelength of maximum absorption of the dye complex with nucleic acid, such as an ultraviolet or visible lamp, an arc lamp, a laser, or even sunlight. The dyes of the present invention are preferably excited at a wavelength between about 450 nm and about 550 nm.

Preparation of the cells for observation optionally includes washing the cells to remove background fluorescence or other reagents. Typically, the suspended solids in a sample are concentrated through filtration or centrifugation and then resuspended in a medium containing a metabolizable carbohydrate, to which an effective amount of dye is then added. The cells are optionally mounted or transferred to an instrument prior to observation; or fixed.

The fluorescent signal of the distinctive complex is detected qualitatively or quantitatively by detection of the resultant light emission at a wavelength at or near the wavelength of maximum emission of the dye, typically greater than about 500 nm. Fluorescence that is green or yellow-green can be separately collected from fluorescence that is red. Fluorescence of single cells can be detected, and if required, quantitated by several means, including visual inspection under a microscope, photographic or video film, automated or semiautomated fluorescence imaging, flow cytometry, fluorescence spectroscopy in a fluorometer, or in a microplate reader, using the appropriate filter(s) or photomultiplier(s).

When combined with an additional detection reagent, such as a cell impermeant counterstain, fluorescent protein, organelle stain, or fluorogenic substrate, the dye and reagent(s) are excited simultaneously or sequentially and the fluorescence is observed using optical filters or monochrometers capable of resolving the fluorescence emission of the dye and the additional detection reagent or reagents.

In one aspect of the invention, the structures are used to analyze the vacuoles present in fungal cells, for example to assess the size or number of vacuoles or to investigate vacuolar processes. In another aspect of the invention the presence of DIS is used to detect the presence of fungal cells in a sample also containing non-fungal cells. In yet another aspect of the invention, the method is used to determine whether both bacteria and live fungal contaminants are present in a sample. For example, fermented wine can be analyzed for living yeast just prior to bottling to screen for a minute amount of yeast that can turn bottled wine to vinegar. Bacterial and dead yeast contaminants are brightly stained (e.g. bright green fluorescence with Compound 591), but only live yeast cells contain the distinctive complex. Bacterial contaminants are distinguished from yeast by size, morphology and fluorescence color (wavelength).

In yet another aspect of the invention, the resulting structures are detected and correlated with cell metabolic activity. Although the lack of formation of the intravacuolar structures in the presence of the dye does not definitively establish the non-viability of the sample cells, the formation of the structures is indicative of some metabolic activity (i.e. viability) of the sample cells. Furthermore, the formation of DIS increases in highly active cells. In another aspect of the invention, the formation of DIS is used to determine the viability of a yeast sample, for example monitoring a spent yeast batch prior to harvesting, typically performed when the population is greater than about 90% dead. A series of samples is taken from the yeast batch and stained to assess viability. The percentage of dead or metabolically inactive cells for the population is calculated based on the percentage of cells lacking the distinctive fluorescent complex in the sample counted.

The presence of the intravacuolar structures can be used to measure the effect of a metabolic effector. The effect of a metabolic effector can be observed over time, or after a fixed period of time. Because the structures do not appear when the cell metabolism is greatly depressed or inactivated, but do appear when such metabolically inactive cells are removed from the inactivating conditions, the dyes of this invention are optionally used to determine whether exposure to a cytotoxic event is lethal or only disabling. Alternatively, the size and amount of structures per cell (or the presence or magnitude of the corresponding fluorescence) is used to monitor cell metabolism. Typically, an increased metabolic rate is reflected in a faster rise in the ratio of the long wavelength fluorescence emission to the short wavelength fluorescence emission. The method can be used to screen for new or existing mains that are abnormally metabolically active or inactive, or are inhibited by selected metabolic effectors (e.g. in the evaluation of fungicides and fungistats) or enhanced by effectors (e.g. in the evaluation of improved fermentation strains). Alternatively, the method of the present invention can be used to maximize or minimize the conditions for growth and/or reproduction.

The examples below are given so as to illustrate the practice of this invention. They are not intended to limit or define the entire scope of this invention. In the structural formulae below, the substituent phenyl is represented by the symbol 527, as is generally used and understood in the art.

EXAMPLE 1

Preparation of 2-chloro-4-[2,3-dihydro-3-methyl-(benzo-1,3-thiazol-2-yl)-methylidene]-1-phenylquinolinium iodide (dye 591)

The following compound is prepared:

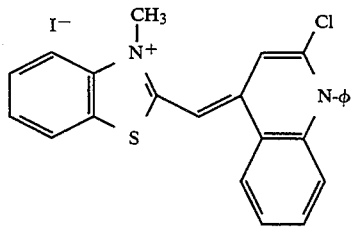

To 2.8 g (11.9 mmoles) of 1,2-dihydro-4-methyl-1-phenyl-2-quinolone in 20 mL of methylene chloride is added, 1.85 g of phosphorus oxycloride and a catalytic amount of dimethylformamide (Marson, TETREAHEDRON., 48, 3659 (1992)). The resulting mixture is heated to reflux for 24 hours. The reaction mixture is cooled to room temperature and 3.5 g (9.6 mmoles) of N-methyl-2-methylthiobenzothiazolium tosylate (Rye, et al., NUCLEIC ACIDS RES., 20, 2803 (1992)) is added followed by 1.3 mL (9.4 mmoles) of triethylamine. The mixture is stirred for an additional 6 hours. The crude product is purified on silica gel using ethyl acetate:chloroform:methanol, 3:3:1 as eluant. The product is then recrystallized from methanol/chloroform/ethyl acetate.

An alternative synthetic route to this product utilizes 4-[2,3-dihydro-3-methyl-(benzo-1,3-thiazol-2-yl)methylidene]-1,2dihydro-1-phenyl-2-quinolone (4), which in turn is prepared from 1,2dihydro-4-methyl-1-phenyl-2-quinolone (1) and 3-methyl-2-methylthiobenzothiazolium tosylate. Thus the lithium enolate of (1) prepared from treating the quinolone with 2.7 equivalent of lithium diisopropyl amide) or the silyl enolate (from (1) and trimethylsilyl trifluoromethanesulfonate and diisopropylcthylamine) is stirred with the benzothiazolium tosylate. The desired intermediate (a quinolone) is isolated by column chromatography. The quinolone is then treated with phosphorous oxychloride to generate the 2-chloro derivative.

EXAMPLE 2

Preparation of 2-bromo-4-[2,3-dihydro-3-methyl-(benzo-1,3-thiazol-2-yl)-methylidene-1-phenylquinolinium iodide (dye 774)

The following compound is prepared:

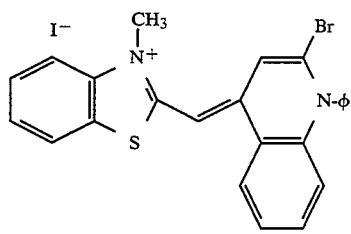

To 0.47 g (2 mmoles) of 1,2-dihydro-4-methyl-1-phenyl-2-quinolone (1) in 8 mL of toluene is added, 0.6 g (2.2 mmoles) of phosphorous tribromide and the solution is heated to reflux for 30 minutes. The mixture is cooled to room temperature, diluted with 20 mL of ethyl acetate and filtered. The solid thus obtained is suspended in 15 mL of methylene chloride and added to a solution of 3-methyl-2-methylthiobenzothiazolium tosylate (0.55 g, 1.5 mmoles) and triethylamine (0.35 mL, 1.8 mmoles) in 8 mL of DMF. The reaction mixture is stirred for 30 minutes and the red solid is separated by filtration. The volatile components of the filtrate are removed under reduced pressure and the residue is purified using a silica gel column, eluting with 3:3:1 ethyl acetate/chloroform/methanol. The red-/orange band that has a slightly higher $R_f$ than the 2-chloro-4-[2,3-dihydro-3-methyl-(benzo-1,3-thiazol-2-yl)-methylidene]-1-quinolinium iodide (Example 1) is isolated, redissolved in about 1.5 mL of methanol and added to 1.5 g of NaI in 20 mL of water. The product is isolated by filtration as the iodide salt and dried in vacuo.

EXAMPLE 3

Preparation of 2-chloro-7-methoxy-4-[(2,3-dihydro-3-methyl-(benzo-1,3-thiazol-2-yl)-methylidene]-1-phenylquinolinium chloride (dye 5103)

The following compound is prepared:

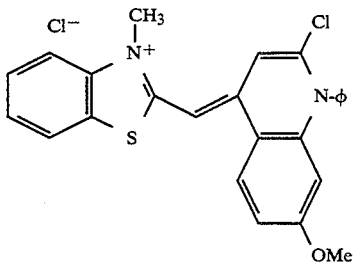

1,2-dihydro-3-methyl-7-methoxy-1-phenyl-2-quinolone (0.53 g, 2 mmoles) is dissolved in 10 mL of methylene chloride with 0.37 g (2.4 mmoles) of phosphorous chloride and 0.05 mL of DMF, and heated to reflux overnight. The mixture is cooled to room temperature and 0.73 g of 3-methyl-2-methylthiobenzothiazolium tosylate is introduced followed by 0.28 mL (2 mmoles) of triethylamine. The mixture is stirred for 30 minutes and the crude product is purified on a silica gel column eluting with 4:4:1 ethyl acetate/chloroform/methanol to obtain the desired product as the chloride salt.

EXAMPLE 4

Preparation of 2-chloro-4-[3-methyl-2,3-dihydro-(benzo-1,3-thiazole)-2-methylidene]-1-phenylpyridinium chloride (Dye 578)

The following compound is prepared:

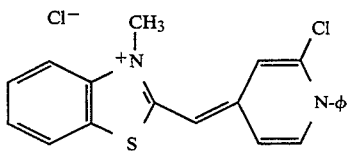

A mixture of 0.37 g (2 mmoles) of 1,2-dihydro-4-methyl-1-phenyl-1-phenyl-2-pyridone, 0.34 g (2.2 mmoles) of phosphorous oxychloride and 0.05 mL of DMF in 5 mL of methylene chloride are heated at 60° C. in a sealed tube overnight. The reaction mixture is cooled to room temperature and another 5 mL of methylene chloride is added, followed by 2 mmoles of 3-methyl-2-methylthiobenzothiazolium tosylate and 2 mmoles of triethylamine. The reaction mixture is stirred at room temperature for 3 hours. The product is isolated by filtration as its chloride salt with a 17% yield.

EXAMPLE 5

Preparation of 2-chloro-4-[2,3-dihydro-3-methyl-(benzo-1,3-thiazol-2-yl)-methylidene]-1-cyclohexylquinolinium tosylate (dye 780)

The following compound is prepared:

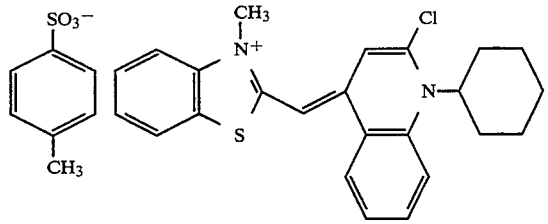

1-Cyclohexyl-1,2-dihydro-4-methyl-2-quinolone is prepared using N-cyclohexylaniline as starting material. The quinolone (0.482 g, 2 mmol) is transformed to the 2-chloro-1-cyclohexylquinolinium chloride with a procedure similar to Example 3, and is then reacted with 3-methyl-2-methylthiobenzothiazolium tosylate (0.74 g, 2 mmol) and triethylamine (0.28 mL, 2 mmol) to yield the product.

EXAMPLE 6

Preparation of 4-[2,3-dihydro-4-methyl-(benzo-1,3-thiazol-2-yl)-methylidene]-1-phenyl-2-trifluoromethanesulfonyloxy-quinolinium iodide (dye 854)

The following compound is prepared:

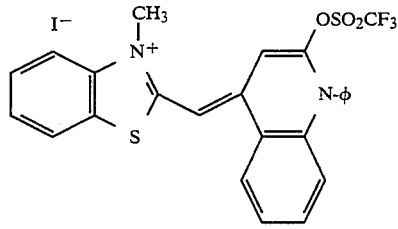

Trifluoromethanesulfonic acid anhydride (66 μL) is introduced to 0.1 g of 1,2-dihydro-4-[2,3-dihydro-3-methyl-(benzo-1,3-thiazol-2-yl)-methylidene]-1-phenyl-2-quinolone (Example 1) in 5 mL of 1,2-dichloroethane, and the solution is heated at 80° C. for 3 hours. The reaction is worked up with water and chloroform, and the resulting product is purified by column chromatography on silica gel.

EXAMPLE 7

Optimization of dye concentration for generation of DIS:

Baker's yeast (*Saccharomyces cerevisiae*) cell cultures are grown overnight in 30–50 mL of Yeast extract Peptone Dextrose broth at 30° C., shaken at 200 rpm in 100 mL serum bottles. Four mL of cells are harvested by centrifugation for 5 minutes at 10,000 Xg and resuspended in 10 mL of sterile 2% glucose with 10 mM Na-HEPES, pH 7.2 (glucose-HEPES). 1.5 mL of cell suspension are added to each of six 1-cm pathlength fluorescence cuvettes containing 7 mm magnetic stir bars.

Four mL of a 60 μM Dye 591 solution in glucose-HEPES (as above) is prepared from a 10 mM DMSO stock solution of Dye 591. Serial 2-fold dilutions of the 60 μM Dye 591 solution are prepared in glucose-HEPES to result in 60, 30, 20, 10, 5, and 2.5 μM Dye 591 solutions. A volume of 1.5 mL of each D is added to 1.5 mL of yeast suspension, resulting in final Dye 591 concentrations from 1.25–30 μM.

Emission spectra of the fluorescence of each yeast suspension with Dye 591 are measured in a Photon Technologies International (PTI) fluoromelet equipped with a stirred, thermoregulated cuvette holder held at a constant 30°±0.2° C. Spectra are acquired every 5 minutes for a total period of 60 minutes. Excitation is at 470 nm and the fluorescence emission is acquired from 500–700 nm. At the end of the experiment, the red/green fluorescence ratio is determined at each time point by dividing the integrated fluorescence at 560–610 nm (red) by that at 510–560 nm (green). The greatest rate of change in red/green fluorescence ratio indicates the most rapid conversion of dye from green uniform stain to red DIS structures. The result of the fluorometric fluorescence ratio determination is confirmed by microscopic observation of DIS in the yeast cells.

EXAMPLE 8

Optimization of cell number for staining of yeast batch fermentation mixtures:

A large batch yeast fermentation mixture is sampled, concentrated by centrifugation for 5 min at 10,000 Xg and resuspended in a sufficient volume of glucose-HEPES to yield a suspension that is just perceptibly turbid by visual inspection. The volume sampled and the volume required to make the final dilution are noted and the ratio of the sampled/diluted (s/d) volume is determined. A second volume of the batch that is equal to 4/(s/d) is then sampled (eg. if 1 mL is sampled and it is diluted in 10 mL to yield a barely turbid suspension, then the volume to be sampled is 4/(1/10) or 40 mL). The new sample is concentrated by centrifugation as described above and resuspended in glucose-HEPES to a final volume of 4 mL. 1.5 mL of this suspension is then diluted serially 1:2 in 6 dilution blanks containing 1.5 mL of glucose-HEPES. The contents of each tube is then transferred to a 1 cm pathlength fluorescence cuvette and 1.5 mL of glucose-HEPES containing 10 $\mu$M Dye 591 added to each to begin the time-course.

Emission spectra of the fluorescence of each yeast suspension with Dye 591 are measured in a Photon Technologies International (PTI) fluorometer equipped with a stirred, thermoregulated cuvette holder held at a constant 30°±0.2° C. Spectra are acquired every 5 minutes for a total period of 60 minutes. Excitation is at 470 nm and the fluorescence emission is acquired from 500–700 nm. At the end of the experiment, the red-/green fluorescence ratio is determined at each time point by dividing the integrated fluorescence at 560–610 nm (red) divided by that at 510–560 nm (green). The greatest rate of change in red/green fluorescence ratio indicates the most rapid conversion of dye from green uniform stain to red DIS structures. The result of the fluorometric fluorescence ratio determination is confirmed by microscopic observation of DIS in the yeast cells.

FIG. 2 represents the relationship between optimal dye concentration and cell number for Saccharomyces yeast stained with Dye 591.

EXAMPLE 9

Temperature optimization for staining of yeast cells using Dye 578:

Baker's yeast (*Saccharomyces cerevisiae*) cell cultures are grown overnight in 30–50 mL of YPD broth at 30° C., shaken at 200 rpm in 100 mL serum bottles. 4 mL of cells are harvested by centrifugation for 5 min at 10,000×g and resuspended in 10 mL of sterile glucose-HEPES. 1.5 mL aliquots of this yeast cell suspension are added to each of six 1 cm pathlength fluorescence cuvettes containing 7 mm magnetic stir bars. A sample of Dye 578 at 10 $\mu$M in glucose-HEPES and pre-equilibrated to the appropriate temperature is added to each cuvette (also pre-equilibrated at the appropriate temperature) to begin the experiment.

The development of increasing red/green (excitation at 480, green emission 490–510, yellow-orange emission 540–560 nm) fluorescence ratio with time of exposure to Dye 578 is determined at a series of temperatures in 10-degree intervals ranging from 10° to 50° C. Emission spectra of the fluorescence of each yeast suspension with Dye 578 are measured in a Photon Technologies International (PTI) fluorometer equipped with a stirred, thermoregulated cuvette holder held at a constant temperature for the duration of each experiment. The temperatures of the experiments are 10°, 20°, 25°, 30°, 40°, and 50°±0.2° C. and are monitored continuously with a thermocouple probe. Spectra are acquired every 5 minutes for a total period of 60 minutes. Excitation is at 480 nm and the fluorescence emission is acquired from 490–600 nm. At the end of the experiment, the red-/green fluorescence ratio is determined at each time point by dividing the integrated fluorescence at 540–560 nm (yellow-orange) by that at 490–510 nm (green). The greatest rate of change in "red/green" fluorescence ratio indicates the most efficient conversion of dye from green uniform stain to yellow-orange DIS structures.

The result of the fluorometric fluorescence ratio determination is confirmed by microscopic observation of DIS in the yeast cells. An example of a similar experiment performed with Dye 591 appears in FIG. 3.

EXAMPLE 10

Pulse-loading of Neurospora crassa with Dye 582:

It is evident that since the DIS-forming dyes are readily removed from the loading solution by yeast (see FIG. 4) a pulse-loading technique is possible with yeast and fungi. *Neurospora crassa* is cultured in YPD broth medium overnight at 30° C. A 50 $\mu$L sample is withdrawn with a variable pipettor and delivered directly into a microfuge tube containing 150 $\mu$L of glucose-HEPES. The sample is incubated at room temperature for 15 minutes and 1.2 mL of a 30 $\mu$M solution of Dye 582 in glucose-HEPES is added. After 5 minutes the sample is centrifuged at 10,000 rpm for 5 min in a microcentrifuge and the pellet resuspended in 100 $\mu$L of fresh glucose-HEPES. The sample is then incubated for 1 hour at 30° C. to develop the DIS. Ten $\mu$L of sample is then withdrawn and observed by fluorescence microscopy using a triple-band DAPI/fluorescein/Texas Red filter set (Omega Optical) to visualize the yellow-orange structures.

EXAMPLE 11.

Cell counting and viability assessment by automated fluorescence microscopy of yeast labeled with Dye 591 and Calcofluor TM White M2R:

Saccharomyces yeast cultured as described in Example 7 can be observed in the microscope using transmitted light (see FIG. 5, step 1). Yeast suspended in glucose-HEPES are stained with 10 $\mu$M Dye 591 for 60 min at 30 ° C. (FIG. 5, step 2). Enough 5 mM Calcofluor TM White M2R (Sigma) stock solution (in water) is added to yield a final concentration of 25 $\mu$M Calcofluor TM White M2R. The mixture is then incubated for an additional 15 minutes (FIG. 5, step 3). The sample is then either centrifuged at 10,000 rpm in the microfuge for 5 min and resuspend in 1 mL of fresh glucose-HEPES and a 30 $\mu$L sample of this suspension is withdrawn, or a 30 $\mu$L sample is taken without washing and added to a microscope slide that has been coated with >100,000 MW poly-L-lysine. The droplet is then trapped between a coverslip and the slide and the edges of the coverslip are sealed with paraffin or other non-toxic sealant.

When observed using a fluorescence microscope equipped with a Hg source and a triple band filter cube (Omega XF-56) the live yeast cells are observed to contain red cylindrical structures and may or may not also contain green diffuse fluorescent stain. All cells show blue fluorescent ring staining due to the binding of Calcofluor TM White M2R. Acquisition and analysis of true color images allows discrimination of metabolically active (live) cells from dead cells.

Fluorescence microscopic images are acquired using a Nikon Diaphot inverted fluorescence microscope with a 100 W Hg source, and 60 X 1.4 NA Plan Apochromat objective lens. Images are acquired using an Optronics high sensitivity color CCD camera optically coupled to the microscope via a 1 projector lens placed in the CCTV port. The red and blue RGB video image components are digitized individually and stored using Image-1 hardware and software from Universal Imaging, Inc. Image analysis is used to define live and dead cells. First the red plane is recalled and a threshold intensity and minimum number of pixels at this intensity are set manually to define areas containing DIS (FIG. 5, step 4A). The blue plane is then recalled and each cell area is defined by its blue ring stain (FIG. 5, step 4B). With the cell areas defined (blue) and the presence of DIS evaluated (red) the coincidence of the two is determined by analysis routines in the image processor. Cells with coincident blue and red staining are counted as active (live) and cells defined in blue but without coincident red staining of sufficient intensity are defined as inactive (dead) (FIG. 5, step 5).

EXAMPLE 12

Detection of individual live and dead fungal cells in whole blood:

Venous blood is drawn aseptically into a heparinized Vacutainer (Becton-Dickinson) and held at 2520 C. until analysis is performed. *Candida pseudotropicalis* cells are added to a final density of $10^6$/mL of blood, which corresponds to at least 1 cell per field (40× objective lens, 10× ocular) in a standard wet-mount preparation. A volume of 250 μL of a balanced salt solution containing 4% dextrose, and 10 mM Na-HEPES (final pH 7.4), is aliquoted into a 1.5 mL microfuge tube and 5 μL of a 10 mM solution of Dye 5103 in DMSO is added. The resulting solution is mixed thoroughly by repipetting and 750 μL of whole blood is added, followed again by vigorous mixing. The suspension is then incubated at 30° C. for 30 min. A 5–10 μL aliquot is removed and trapped between a microscope slide and coverslip.

The fluorescence of the cells is observed using either a combination excitation/emission filter set or by alternating between excitation with a standard fluorescein bandpass filter set and a standard Texas Red filter set. Live, actively metabolizing fungal cells are marked by very short cylindrical to spherical orange-red DIS, while dead cells are stained uniformly yellow-green. White blood cells such as neutrophils and lymphocytes exhibit primarily green nuclear fluorescence, but some cytoplasmic signal is also seen. Erythrocytes provide virtually no background fluorescence; indeed the background of erythrocytes appears in negative contrast to a low level green emission from non-specific binding of Dye 5103 to the glass surfaces.

EXAMPLE 13

Combined measurement of carbohydrate utilization in yeast cultures using a fluorescence microplate reader:

Baker's yeast (*Saccharomyces cerevisiae*) cell cultures am grown overnight in 30–50 mL of YPD broth at 30° C., shaken at 200 rpm in 100 mL serum bottles. The staining of the yeast is optimized (see Example 1) for $5 \times 10^6$ cells/mL. Five mL of cells (approximately $2 \times 10^7$/mL) are harvested by centrifugation for 5 minutes at 10,000 Xg and resuspended in 10 mL ($1 \times 10^7$/mL) of sterile 100 mM 2-deoxyglucose, 10 mM Na-HEPES, pH 7.2 in water. The cell suspension is incubated overnight on a rotator at 30° C., harvested by centrifugation, and resuspended in an equivalent volume of HEPES-buffered water (pH 7.2).

Two 96-well plates are selected, one with a round-bottom, the other with a flat bottom. 100 μL of yeast cell suspension ($10^7$ cells/mL, $10^6$ cells/well) is added to wells in columns 1–11, rows A–G in the flat-bottom plate. 100 μL of HEPES-buffered water is pipetted into all 8 wells of column 12 and all wells in row H. Tests of 11 two-fold serially-diluted carbohydrate solutions are carried out in triplicate (rows A–C) and compared to a control series of D-glucose dilutions, which are also performed in triplicate (rows D–F). Controls for dye and yeast alone, plus and minus carbohydrate are carried out in rows G & H.

Dye 591 and carbohydrate solutions are prepared in a separate round-bottom 96-well plate as follows: 150 μL of a 4× concentrate of the highest desired concentration of test carbohydrate or glucose solution is added to the wells in column 1, rows A–C and D–H, respectively. 75 μL of HEPES-buffered water is pipetted into the wells in column 2–12, rows A–F & H (not G) 150 μL of HEPES-buffered water is added to all wells in row G. The carbohydrate solutions are diluted 1:2 consecutively from column 2–11 by transferring 75 μL volumes and discarding the residual 75 μL from column 11. 75 μL of a 4X concentrated solution of Dye 591 in Na-HEPES-buffered water is then added to the wells in columns 1–12 and rows A–F & H (not G). The plates are both covered and cooled to 15° C. for 20 minutes. 100 μL of the solutions in every row and column of the round-bottom well plate is added to the yeast suspensions in the flat-bottom plate with an 8-channel pipettor.

The fluorescence is read immediately at two wavelengths: 485 nm excitation/530 nm emission (GREEN) and 470 excitation/620 nm emission (RED). The plates are incubated at 30° C. on a rotating shaker (300 rpm) and read every 10 min for 2 hours. If wells containing yeast alone or dye alone exhibit significant fluorescence, the test well fluorescence values are corrected by subtraction of the "control" fluorescent intensity. The RED/GREEN ratio is calculated for each well at each time point and the rate of increase of each is compared. The optimal conditions for DIS formation are defined as the conditions under which a maximum change in RED/GREEN ratio occurs over time. This is expressed as the maximum rate of change in R/G ratio for test carbohydrate divided by the maximum rate of change in R/G ratio for glucose, quantity multiplied by 100. This yields the % activity relative to an equivalent concentration of glucose.

FIG. 6 represents the change in fluorescence ratio at a single concentration of glucose as described in this example. Fluorescence of Dye 591 and the pH indicator DM-NERF is measured in a fluorescence microplate reader. The drop in pH measured by a decrease in DM-NERF fluorescence parallels the formation of DIS that is indicated by a change in the red/green fluorescence ratio.

EXAMPLE 14

Detection of yeast in wine products:

A solution containing 8% glucose, 40 mM Na-HEPES, 20 uM Dye 591 is prepared in sterile distilled water. A 0.75 mL sample of wine is mixed with 0.25 mL of dye solution (1:4 v/v) and incubated for 60 rain at 30° C. A wet-mount slide is prepared by trapping 10 μL of the wine+staining solution between a slide and coverslip. The preparation is observed by fluorescence microscopy using a fluorescence long-pass filter set, and a 10× objective lens to find potential contaminants, live or dead, then with 40× and 100× objectives to confirm and identify the putative contaminant. Dead yeast exhibit yellow-green fluorescence while live yeast are fluorescent green or clear with orange-red DIS. Live or dead bacteria stain with green fluorescence.

It is to be understood that, while the foregoing invention has been described in detail by way of illustration and example, numerous modifications, substitutions, and alterations are possible without departing from the spirit and scope of the invention as described in the following claims.

What is claimed is:

1. A method of forming distinctive intravacuolar structures in fungal cells comprising:

a) combining a sample that contains fungal cells with a staining solution comprising a dye of the formula

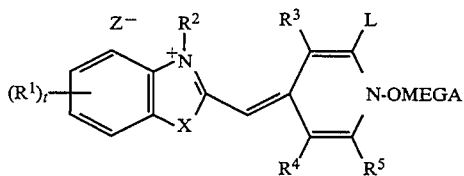

wherein
   each $R^1$ is independently H; or an alkyl group having from 1-6 carbons; or a trifluoromethyl; or a halogen; or $-OR^6$, $-SR^6$ or $-NR^6R^7$ where $R^6$ and $R^7$, which can be the same or different, are independently H; or alkyl groups having 1-6 carbons; or 1-2 alicyclic, heteroalicyclic, aromatic or heteroaromatic rings, containing 1-6 heteroatoms, wherein the heteroatoms are O, N or S; or $R^6$ and $R7$ taken in combination are $-(CH_2)_2-M-(CH_2)_2-$ where M = a single bond, $-O-$, $-CH_2-$, or $-NR^8-$ where $R^8$ is H or an alkyl group having 1-6 carbons; and t = 1-4;

$R^2$ is an alkyl group having 1-6 carbons;

X is O, S, Se or $NR^9$, where $R^9$ is H or an alkyl group having 1-6 carbons; or X is $CR^{10}R^{11}$ where $R^{10}$ and $R^{11}$, which may be the same or different, are independently alkyl groups having 1-6 carbons, or $R^{10}$ and $R^{11}$ taken in combination complete a five or six membered saturated ring;

$R^3$, $R^4$ and $R^5$, which may be the same or different, are independently H; or an alkyl, alkenyl, polyalkenyl, alkynyl or polyalkynyl group having 1-6 carbons; or a halogen; or $-OR^6$, $-SR^6$ or $-(NR^6R^7)$; or $R^4$ and $R^5$, taken in combination, have the formula

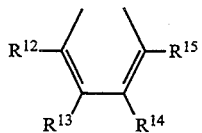

forming a quinolinium ring system; wherein
   $R^{12}$, $R^{13}$, $R^{14}$ and $R^{15}$ are independently H; or an alkyl, alkenyl, polyalkenyl, alkynyl or polyalkynyl group having 1-6 carbons; or a halogen; or $-OR^6$, $-SR^6$ or $-(NR^6R^7)$;

$Z^-$ is a biologically compatible counterion;

L is Cl, Br, I, F, or $-OSO_2R^{16}$ where $R^{16}$ is alkyl having 1-6 carbons, or perfluoroalkyl having 1-6 carbons, or aryl; and OMEGA is a cyclic substituent that has a total of 2-16 ring carbon atoms in 1-2 alicyclic, heteroalicyclic, aromatic, or heteroaromatic rings, containing 1-4 heteroatoms wherein the heteroatoms are O, N or S, that is unsubstituted or optionally substituted one or more times, independently, by halogen, alkyl, perfluoroalkyl, amino, alkylamino, dialkylamino, or alkoxy, having 1-6 carbons;

where the dye is present in an amount sufficient to give a distinctive intravacuolar structure or structures; and b) allowing sufficient time for the dye to combine with one or more cells in the sample and form the distinctive intravacuolar structure or structures.

2. The method of claim 1, wherein the dye forms one or more fluorescent intravascular structures.

3. The method of claim 2, wherein the fungal cells are yeast cells.

4. The method of claim 2, further comprising adding to the sample an additional detection reagent selected from the group consisting of a fluorophore, luminophore, radioactive isotope, free radical, enzyme, coenzyme, hapten, protein, nucleic acid, microparticle, liposome, metal, chelate, magenetic material, electrophore, electrochemiphore, chromophore, and a labeled specific binding pair member for detection of a specific cell component, intracellular substances, or cellular condition wherein said additional detection reagent does not complete inhibit formation of the intravacuolar structures.

5. The method of claim 1, wherein the sample contains mutant fungal cells or transformed fungal cells.

6. The method of claim 1, wherein the formation of intravacuolar structures stops a plurality of the cells from growing or reproducing.

7. The method of claim 6, further comprising washing the cells and placing the cells in fresh media.

8. The method of claim 1, wherein the sample has been exposed to a metabolic effector.

9. The method of claim 1, wherein the sample contains both fungal and non-fungal cells.

10. The method of claim 1, wherein the dye has the structure

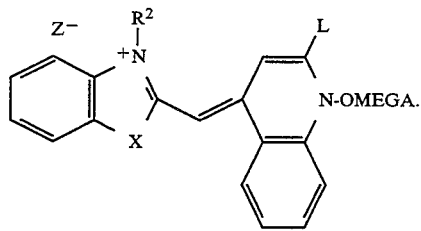

11. The method of claim 1, wherein OMEGA is a substituted or unsubstituted cyclohexyl, cyclohexenyl, morpholino, piperidinyl, naphthyl, phenyl, thienyl, benzothiazolyl, furanyl, oxazolyl, benzoxazolyl or pyridinyl.

12. The method of claim 1, wherein the sample contains one or more yeast cells that are combined with the dye having the structure

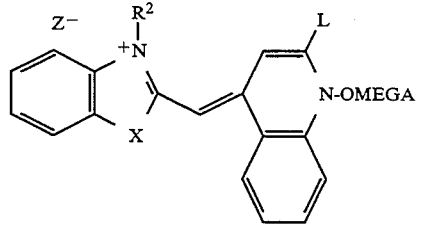

wherein
X is O or S;
R² is an alkyl group having 1-6 carbons;
L is Cl, Br, or I;
and OMEGA is a substituted or unsubstituted naphthyl, phenyl, thienyl, morpholino, or cyclohexyl;
where said dye is present in the staining solution in a concentration of greater than about 1 μM; and where after about 10 minutes the dye forms a fluorescent intravacuolar structure or structures.

13. A method of analyzing the metabolic activity of fungal cells, comprising:
a) combining a sample containing fungal cells with a staining solution comprising a dye of the formula

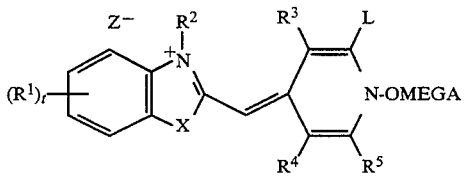

wherein
each R¹ is independently H; or an alkyl group having from 1-6 carbons; or a trifluoromethyl; or a halogen; or —OR⁶, —SR⁶, or —NR⁶R⁷ where R⁶ and R⁷, which are the same or different, are independently H; or alkyl groups having 1-6 carbons; or 1-2 alicyclic, heteroalicyclic, aromatic or heteroaromatic rings, containing 1-4 heteroatoms, wherein the heteroatoms are O, N or S; or R⁶ and R⁷ taken in combination are —(CH₂)₂—M—(CH₂)₂— where M=a single bond, —O—, —CH₂—, or —NR⁸— where R⁸ is H or an alkyl group having 1-6 carbons; and t=1-4;
R² is an alkyl group having 1-6 carbons;
X is O or S;
R³, R⁴ and R⁵, which may be the same or different, are independently H; or an alkyl, alkenyl, polyalkenyl, alkynyl or polyalkynyl group having 1-6 carbons; or a halogen; or —OR⁶, —SR⁶ or —(NR⁶R⁷); or R⁴ and R⁵, taken in combination, have the formula

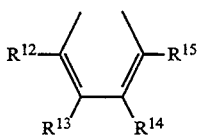

forming a quinolinium ring system; wherein
R¹², R¹³, R¹⁴ and R¹⁵ are independently H; or an alkyl, alkenyl, polyalkenyl, alkynyl or polyalkynyl group having 1-6 carbons; or a halogen; or —OR⁶, —SR⁶ or —(NR⁶R⁷); or R⁴ and R⁵, taken in combination, have the formula

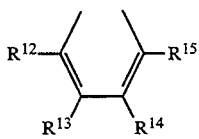

forming a quinolinium ring system; wherein
R¹², R¹³, R¹⁴ and R¹⁵ are independently H; or an alkyl, alkenyl, polyalkenyl, alkynyl or polyalkynyl group having 1-6 carbons; or a halogen; or —OR⁶; —SR⁶ or —(NR⁶R⁷);
Z⁻ is a biologically compatible counterion;
L is Cl, Br, I, F, or —OSO₂R¹⁶ where R¹⁶ is alkyl having 1-6 carbons, or perfluoroalkyl having 1-6 carbons, or aryl; and
OMEGA is a cyclic substituent that has a total of 2-16 ring carbon atoms in 1-2 alicyclic, heteroalicyclic, aromatic, or heteroaromatic rings, containing 1-4 heteroatoms wherein the heteroatoms are O, N or S, that is unsubstituted or optionally substituted one or more times, independently, by halogen, alkyl, perfluoroalkyl, amino, alkylamino, dialkylamino, or alkoxy having 1-6 carbons;
where the dye is present in an amount sufficient to give a distinctive intravacuolar structure or structures;
b) allowing sufficient time for the dye to combine with one or more cells in the sample and form the distinctive intravacuolar structure or structures;
c) illuminating the sample;
d) detecting the presence of a distinctive intravacuolar structure or structures in the fungal cells; and
e) correlating presence or magnitude of the distinctive intravacuolar structure or structures with metabolic activity of the fungal cells.

14. The method of claim 13, wherein the distinctive intravacuolar structures are detected by a fluorescence response resulting from illumination; and
the presence or magnitude of the fluorescence response resulting from illumination is correlated with metabolic activity of the fungal cells.

15. The method of claim 14, wherein the dye has the structure

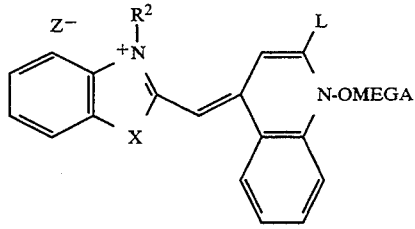

wherein OMEGA is a substituted or unsubstituted cyclohexyl, cyclohexenyl, morpholino, piperidinyl, naphthyl, phenyl, thienyl, furanyl, or pyridinyl.

16. The method of claim 15, where the sample has been exposed to a metabolic effector that is a chemical reagent, a biological agent, or an environmental condition where the presence or magnitude of the fluorescence response is indicative of the effector's ability to enhance or inhibit metabolism.

17. The method of claim 15, wherein the fungal cells are yeast cells.

18. The method claim 17, wherein the correlation of the fluorescence response with metabolic activity of the fungal cells is used to screen mutant or transformed strains of yeast.

19. The method of claim 14, further comprising adding to the sample an additional detection reagent selected from the group consisting of a fluorophore, luminophore, radioactive isotope, free radical, enzyme, coenzyme, hapten, protein, nucleic acid, microparticle, liposome, metal, chelate, magnetic material, electrophore, electrochemiphore, chromophore, and a labeled specific binding pair member for detection of a specific cell component, intracellular substances, or cellular condition wherein said additional detection reagent has a fluorescence response that is detectably different from that of the fluorescent intravacuolar structures.

20. The method of claim 14, wherein OMEGA is a substituted or unsubstituted naphthyl, phenyl, thienyl, morpholino, or cyclohexyl and is present in the staining solution in a concentration of greater than about 1 μM.

21. The method of claim 20, wherein the dye has the structure

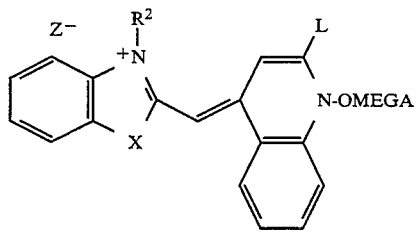

wherein
X is O or S;
$R^2$ is an alkyl group having 1-6 carbons;
L is Cl, Br, or I;
and OMEGA is a substituted or unsubstituted naphthyl, phenyl, thienyl, morpholino, or cyclohexyl.

22. The method of claim 21, wherein the sample also contains an amount of metabolizable carbohydrate greater than 0 and less than about 25 percent weight-/volume.

23. The method of claim 13, wherein the method is used to optimize conditions for minimal activity of said fungal cells.

24. The method of claim 13, wherein the method is used to optimize conditions for maximal metabolic activity or growth of said fungal cells.

25. A method of detecting fungal cells, comprising
a) combining a sample thought to contain one or more fungal cells with a staining solution comprising a dye of the formula

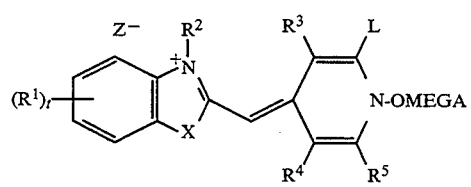

wherein
each $R^1$ is independently H; or an alkyl group having from 1-6 carbons; or a trifluoromethyl; or a halogen; or —$OR^6$, —$SR^6$ or —$(NR^6R^7)$ where $R^6$ and $R^7$, which can be the same or different, are independently H; or alkyl groups having 1-6 carbons; or 1-2 alicyclic, heteroalicyclic, aromatic or heteroaromatic rings, containing 1-6 heteroatoms, wherein the heteroatoms are O, N or S; or $R^6$ and $R^7$ taken in combination are —$(CH_2)_2$—M—$(CH_2)_2$— where M=a single bond, —O—, —$CH_2$, or —$NR^8$— where $R^8$ is H or an alkyl group having 1-6 carbons; and t=1-4;
$R^2$ is an alkyl group having 1-6 carbons;
X is O, S, Se or $NR^9$, where $R^9$ is H or an alkyl group having 1-6 carbons; or X is $CR^{10}R^{11}$ where $R^{10}$ and $R^{11}$, which may be the same or different, are independently alkyl groups having 1-6 carbons, or $R^{10}$ and $R^{11}$ taken in combination complete a five or six membered saturated ring;
$R^3$, $R^4$ and $R^5$, which may be the same or different, are independently H; or an alkyl, alkenyl, polyalkenyl, alkynyl or polyalkynyl group having 1-6 carbons; or a halogen; or —$OR^6$, —$SR^6$ or —$(NR^6R^7)$; or $R^4$ and $R^5$, taken in combination, have the formula

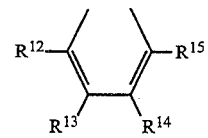

ps forming a quinolinium ring system; wherein
$R^{12}$, $R^{13}$, $R^{14}$ and $R^{15}$ are independently H; or an alkyl, alkenyl, polyalkenyl, alkynyl or polyalkynyl group having 1-6 carbons; or a halogen; or —$OR^6$, —$SR^6$ or —$(NR^6R^7)$;
$Z^-$ is a biologically compatible counterion;
L is Cl, Br, I, F, or —$OSO_2R^{16}$ where $R^{16}$ is alkyl having 1-6 carbons, or perfluoroalkyl having 1-6 carbons, or aryl; and
OMEGA is cyclic substituent that has a total of 2-16 ring carbon atoms in 1-2 alicyclic, heteroalicyclic, aromatic, or heteroaromatic rings, containing 1-4 heteroatoms (wherein the heteroatoms are O, N or S), that is unsubstituted or optionally substituted one or more times, independently, by halogen, alkyl, perfluoroalkyl, amino, alkylamino, dialkylamino, or alkoxy having 1-6 carbons;
where the dye is present in an amount sufficient to give a distinctive intravacuolar structure or structures;
b) allowing sufficient time for the dye to combine with said fungal cells in the sample and form the distinctive intravacuolar structure or structures;
c) illuminating the sample; and
d) detecting the presence of cells containing said distinctive intravacuolar structure or structures.

26. The method of claim 25, wherein the presence of cells containing said distinctive intravacuolar structures is detected using transmitted light microscopy.

27. The method of claim 25, where the dye forms one or more distinctive intravacuolar structures that, when illuminated at a suitable absorption wavelength, give a fluorescence response resulting from illumination; and
the presence of cells containing said distinctive intravacuolar structure or structures is detected using means for detecting said fluorescence response resulting from illumination.

28. The method of claim 27, wherein the sample also contains non-fungal cells.

29. The method of claim 27, wherein said means for detecting said fluorescence response is capable of collecting fluorescence emissions from the sample at two or more wavelengths.

30. The method of claim 29, wherein the fluorescence emissions collected at two or more wavelengths are analyzed using ratiometric analysis.

31. The method of claim 27, wherein said means for detecting said fluorescence response is a fluorometer or fluorescence plate reader.

32. The method of claim 27, wherein said means for detecting said fluorescence response is a flow cytometer.

33. The method of claim 27, further comprising sorting the fungal cells based on their fluorescence.

34. The method of claim 27, wherein the fungal cells are selected from the group consisting of Saccharomyces, Candida, and Neurospora cells and the dye, which is present in the staining solution in a concentration of greater than about 1 μM, has the structure:

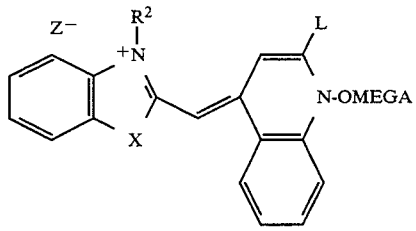

wherein X is O or S;
R² is an alkyl group having 1–6 carbons;
L, is Cl, Br, or I; and
OMEGA is a substituted or unsubstituted naphthyl, phenyl, thienyl, morpholino, or cyclohexyl.

35. The method of claim 34, further comprising adding to the sample an additional detection reagent selected from the group consisting of a fluorphore, luminophore, radioactive isotope, free radical, enzyme, coenzyme, hapten, protein, nucleic acid, microparticle, liposome, metal, chelate, magnetic material, electrophore, electrochemiphore, chromophore, and a labeled specific binding pair member for detection of a specific cell component, intracellular substances, or cellular condition.

* * * * *

UNITED STATES PATENT AND TRADEMARK OFFICE
CERTIFICATE OF CORRECTION

PATENT NO. : 5,445,946
DATED : August 29, 1995
INVENTOR(S) : Bruce L. Roth et al.

It is certified that error appears in the above-indentified patent and that said Letters Patent is hereby corrected as shown below:

At Col. 4, line 31, "having 14 carbons" should be --having 1-6 carbons--.

At Col. 9, line 31, "markers of organdies because of" should be --markers of organelles because of--.

At Col. 15, line 29, "by the symbol 527, as is generally used" should be --by the symbol Ø, as is generally used--.

At Col. 18, line 39, "of each D is added" should be --of each Dye 591 dilution is added--.

At Col. 20, line 65, "microscope via a 1 projector lens" should be --microscope via a 1X projector lens--.

At Col. 21, line 19, "and held at 2520 C." should be --and held at 25 °C.--

At Col. 22, line 58, "and incubated for 60 rain at 30°" should be --and incubated for 60 min at 30°--.

At Col. 23, line 29, "containing 1-6 heteroatoms" should be --containing 1-4 heteroatoms--.

At Col. 27, line 58, "containing 1-6 heteroatoms" should be --containing 1-4 heteroatoms--.

UNITED STATES PATENT AND TRADEMARK OFFICE
CERTIFICATE OF CORRECTION

PATENT NO. : 5,445,946
DATED : August 29, 1995
INVENTOR(S) : Bruce L. Roth et al.

It is certified that error appears in the above-indentified patent and that said Letters Patent is hereby corrected as shown below:

At. Col. 27, line 61, "bond, —O—, —CH$_2$, or" should be --bond, —O—, —CH$_2$—, or--.

At Col. 28, line 16, "ps forming a quinolinium ring" should be --forming a quinolinium ring--.

Signed and Sealed this

Tenth Day of March, 1998

*Attest:*

BRUCE LEHMAN

*Attesting Officer*   Commissioner of Patents and Trademarks